(12) United States Patent
Ikeda et al.

(10) Patent No.: US 11,595,594 B2
(45) Date of Patent: Feb. 28, 2023

(54) IMAGING APPARATUS AND ELECTRONIC DEVICE

(71) Applicant: Semiconductor Energy Laboratory Co., Ltd., Kanagawa-ken (JP)

(72) Inventors: Takayuki Ikeda, Kanagawa (JP); Yusuke Negoro, Osaka (JP)

(73) Assignee: Semiconductor Energy Laboratory Co., Ltd.

( * ) Notice: Subject to any disclaimer, the term of this patent is extended or adjusted under 35 U.S.C. 154(b) by 0 days.

(21) Appl. No.: 17/282,129

(22) PCT Filed: Oct. 7, 2019

(86) PCT No.: PCT/IB2019/058506
§ 371 (c)(1),
(2) Date: Apr. 1, 2021

(87) PCT Pub. No.: WO2020/075031
PCT Pub. Date: Apr. 16, 2020

(65) Prior Publication Data
US 2021/0377463 A1    Dec. 2, 2021

(30) Foreign Application Priority Data
Oct. 11, 2018    (JP) .............................. JP2018-192666

(51) Int. Cl.
*H04N 5/33* (2006.01)
*A61B 5/00* (2006.01)
(Continued)

(52) U.S. Cl.
CPC ............. *H04N 5/33* (2013.01); *A61B 5/0075* (2013.01); *H01L 27/288* (2013.01); *A61B 5/489* (2013.01); *G06V 40/10* (2022.01); *G06V 40/14* (2022.01)

(58) Field of Classification Search
CPC .................. A61B 5/0075; A61B 5/489; G06K 2009/00932; G06K 9/00885;
(Continued)

(56) References Cited

U.S. PATENT DOCUMENTS 8,378,391 B2    2/2013    Koyama et al.
8,916,869 B2    12/2014    Koyama et al.
(Continued)

FOREIGN PATENT DOCUMENTS

CN    102597930 A    7/2012
CN    102598269 A    7/2012
(Continued)

OTHER PUBLICATIONS

International Search Report (Application No. PCT/IB2019/058506) dated Dec. 24, 2019.
(Continued)

*Primary Examiner* — Masum Billah
(74) *Attorney, Agent, or Firm* — Husch Blackwell LLP

(57) ABSTRACT

An imaging apparatus including a light source is provided. The imaging apparatus includes a light-emitting device and a photoelectric conversion device in a pixel, and a pixel circuit has a function of outputting third data generated by multiplying obtained first data by second data (weight). Calculating the third data externally enables more detailed information on a subject with respect to a specific wavelength to be obtained. In addition, reading out collectively a plurality of pixels to which proper weight is given enables output of difference data between pixels and the like, which allows external calculation to be omitted.

16 Claims, 18 Drawing Sheets

(51) Int. Cl.
*H01L 27/28* (2006.01)
*G06V 40/10* (2022.01)
*G06V 40/14* (2022.01)

(58) Field of Classification Search
CPC ........ H01L 27/288; H04N 5/33; H04N 5/378; H04N 5/3575; H04N 5/374; H04N 5/3577; H04N 9/04557; H04N 5/3742; H04N 5/32; H04N 5/3355; H04N 5/345
USPC ......................................................... 348/164
See application file for complete search history.

(56) References Cited

U.S. PATENT DOCUMENTS

| | | | |
|---|---|---|---|
| 9,055,245 B2 | 6/2015 | Kozuma | |
| 9,331,112 B2 | 5/2016 | Koyama et al. | |
| 9,748,291 B2 | 8/2017 | Ikeda et al. | |
| 9,773,814 B2 | 9/2017 | Koyama et al. | |
| 9,773,832 B2 | 9/2017 | Kurokawa | |
| 9,848,144 B2 | 12/2017 | Okamoto et al. | |
| 9,876,946 B2 | 1/2018 | Ikeda | |
| 2002/0060284 A1* | 5/2002 | Mizuno | H04N 5/378 348/E5.079 |
| 2011/0108836 A1 | 5/2011 | Koyama et al. | |
| 2011/0109591 A1 | 5/2011 | Kurokawa et al. | |
| 2012/0241895 A1* | 9/2012 | Kurogi | H01L 27/14612 257/437 |
| 2017/0324916 A1* | 11/2017 | Sugawa | H04N 5/37452 |
| 2020/0091214 A1 | 3/2020 | Ikeda | |
| 2020/0169683 A1 | 5/2020 | Yamamoto | |

FOREIGN PATENT DOCUMENTS

| | | |
|---|---|---|
| EP | 3 051 588 A1 | 8/2016 |
| JP | 2011-118887 A | 6/2011 |
| JP | 2011-119711 A | 6/2011 |
| JP | 2018-136491 A | 8/2018 |
| JP | 2018136491 A * | 8/2018 |
| KR | 2012-0091294 A | 8/2012 |
| WO | WO 2011/055626 A1 | 5/2011 |
| WO | WO 2011/055637 A1 | 5/2011 |

OTHER PUBLICATIONS

Written Opinion (Application No. PCT/IB2019/058506) dated Dec. 24, 2019.

* cited by examiner

| | | | | | | | |
|---|---|---|---|---|---|---|---|
| Line[1] | Rn-1 | En | | Rn | En+1 | | |
| Line[2] | En-1 | Rn-1 | En | Rn | En+1 | | |
| Line[3] | En-1 | Rn-1 | En | Rn | | En+1 | |
| ⋮ | | | | | | | |
| Line[M] | En-1 | | Rn-1 | En | | Rn | |

FIG. 4B

| | | | | | |
|---|---|---|---|---|---|
| Line[1] | En | Rn | | | En+1 |
| Line[2] | En | | Rn | | En+1 |
| Line[3] | En | | Rn | | En+1 |
| ⋮ | | | | | |
| Line[M] | En | | | Rn | En+1 |

FIG. 17A1
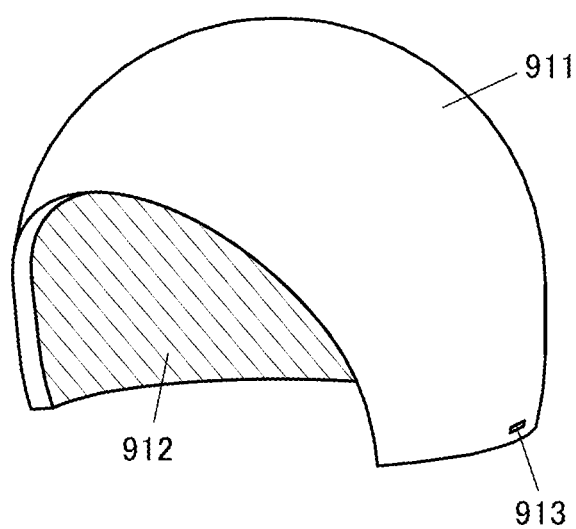
FIG. 17A2
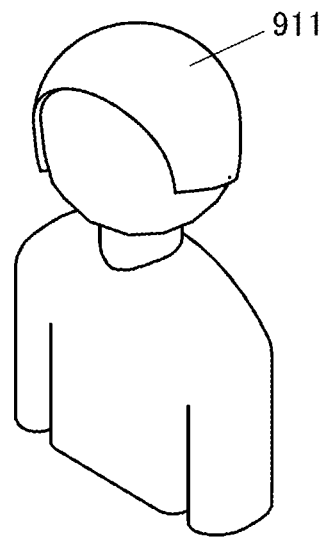
FIG. 17B1
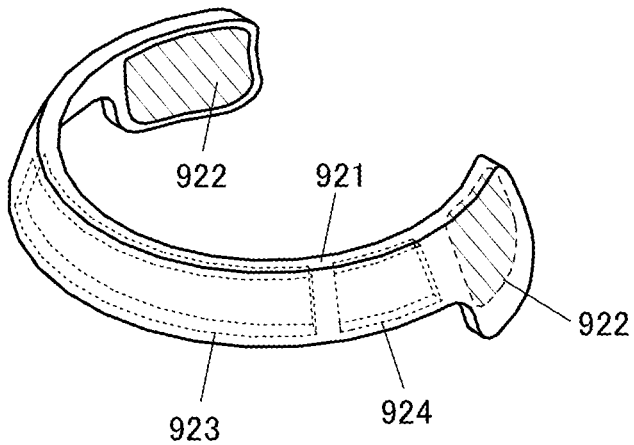
FIG. 17B2
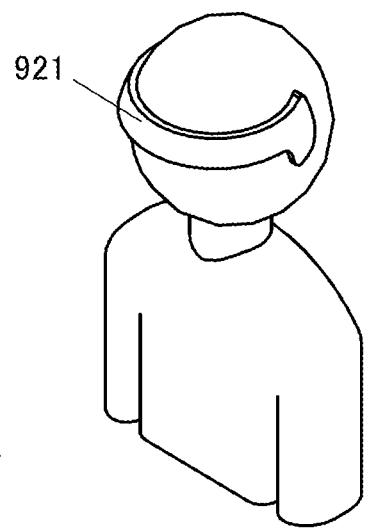

IMAGING APPARATUS AND ELECTRONIC DEVICE

This application is a 371 of international application PCT/IB2019/058506 filed on Oct. 7, 2019 which is incorporated herein by reference.

TECHNICAL FIELD

One embodiment of the present invention relates to an imaging apparatus.

Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. More specifically, examples of the technical field of one embodiment of the present invention disclosed in this specification include a semiconductor device, a display device, a liquid crystal display device, a light-emitting apparatus, a lighting device, a power storage device, a memory device, an imaging apparatus, a driving method thereof, and a manufacturing method thereof.

In this specification and the like, a semiconductor device generally means a device that can function by utilizing semiconductor characteristics. A transistor and a semiconductor circuit are embodiments of semiconductor devices. In some cases, a memory device, a display device, an imaging apparatus, or an electronic device includes a semiconductor device.

BACKGROUND ART

A technique for forming a transistor by using an oxide semiconductor thin film formed over a substrate has attracted attention. For example, an imaging apparatus with a structure in which a transistor including an oxide semiconductor and having an extremely low off-state current is used in a pixel circuit is disclosed in Patent Document 1.

REFERENCE

Patent Document

[Patent Document 1] Japanese Published Patent Application No. 2011-119711

SUMMARY OF THE INVENTION

Problems to be Solved by the Invention

Imaging apparatuses are used as a means not only for visualizing visible light but also for various other purposes. For example, they are used for personal authentication, failure analysis, medical diagnosis, and security purpose. For these purposes, short-wavelength light such as X rays, long-wavelength light such as infrared rays, and the like, as well as visible light are used in accordance with the purpose.

Although natural light or a room light is sometimes used as visible light and infrared rays, the use of a dedicated light source has also become common. A light bulb type lamp, an LED, laser, or the like is often used as the light source; however, they have difficulty in miniaturization and thinning when they are combined with imaging apparatuses.

In view of the above, an object of one embodiment of the present invention is to provide an imaging apparatus including a light source. Another object is to provide an imaging apparatus that includes a thin light source and captures an image from light emitted from the light source and reflected by a subject. Another object is to provide an imaging apparatus including a thin infrared light source. Another object is to provide an imaging apparatus capable of product-sum operation of a plurality of pixels.

Another object is to provide an imaging apparatus with low power consumption. Another object is to provide an imaging apparatus capable of capturing an image at high speed. Another object is to provide an imaging apparatus with high reliability. Another object is to provide a novel imaging apparatus. Another object is to provide a method for operating the above imaging apparatus. Another object is to provide a novel semiconductor device or the like.

Note that the description of these objects does not preclude the existence of other objects. One embodiment of the present invention does not have to achieve all these objects. Other objects are apparent from and can be derived from the description of the specification, the drawings, the claims, and the like.

Means for Solving the Problems

One embodiment of the present invention relates to a thin imaging apparatus including a light source. Alternatively, one embodiment of the present invention relates to an imaging apparatus capable of performing operation.

One embodiment of the present invention is an imaging apparatus including a first pixel, a second pixel, a first correlated double sampling circuit, a second correlated double sampling circuit, and an A/D converter circuit. The first pixel and the second pixel each include a light-emitting device and a photoelectric conversion device. The first pixel is electrically connected to the first correlated double sampling circuit. The second pixel is electrically connected to the first correlated double sampling circuit. The first correlated double sampling circuit is electrically connected to the second correlated double sampling circuit. The second correlated double sampling circuit is electrically connected to the A/D converter circuit. The first pixel, the second pixel, the first correlated double sampling circuit, and the second correlated double sampling circuit include a transistor containing a metal oxide in a channel formation region.

The first pixel and the second pixel may each include a first transistor as the transistor, a second transistor, a third transistor, a fourth transistor, and a fifth transistor. The first pixel and the second pixel may each further include a first capacitor, a second capacitor, and a memory circuit. One of a source and a drain of the first transistor may be electrically connected to one electrode of the photoelectric conversion device. The other of the source and the drain of the first transistor may be electrically connected to one electrode of the first capacitor. The one electrode of the first capacitor may be electrically connected to one of a source and a drain of the second transistor. The other of the source and the drain of the second transistor may be electrically connected to one of a source and a drain of the third transistor. The one of the source and the drain of the third transistor may be electrically connected to one electrode of the second capacitor. The one electrode of the second capacitor may be electrically connected to a gate of the fourth transistor. One of a source and a drain of the fourth transistor may be electrically connected to one of a source and a drain of the fifth transistor. The other of the source and the drain of the fifth transistor may be electrically connected to the first correlated double sampling circuit. The other electrode of the second capacitor may be electrically connected to the memory circuit.

The memory circuit may include a sixth transistor, a seventh transistor, an eighth transistor, and a ninth transistor. The memory circuit may further include a third capacitor. One of a source and a drain of the sixth transistor may be electrically connected to one electrode of the third capacitor. The one electrode of the third capacitor may be electrically connected to a gate of the seventh transistor. One of a source and a drain of the seventh transistor may be electrically connected to one of a source and a drain of the eighth transistor. The other of the source and the drain of the seventh transistor may be electrically connected to one of a source and a drain of the ninth transistor. The one of the source and the drain of the ninth transistor may be electrically connected to the other electrode of the second capacitor.

A structure may be employed in which the other of the source and the drain of the fifth transistor included in the first pixel and the other of the source and the drain of the fifth transistor included in the second pixel are electrically connected to each other and a gate of the fifth transistor included in the first pixel and a gate of the fifth transistor included in the second pixel are electrically connected to each other.

A structure may be employed in which a first wavelength<a second wavelength, the light-emitting devices included in the first pixel and the second pixel emit near-infrared light including the first wavelength and the second wavelength, the photoelectric conversion device included in the first pixel has an absorption edge wavelength shorter than the second wavelength, and the photoelectric conversion device included in the second pixel has an absorption edge wavelength longer than or equal to the second wavelength.

A structure may be employed in which a first wavelength<a second wavelength, the light-emitting device included in the first pixel emits near-infrared light having a peak at the first wavelength, the light-emitting device included in the second pixel emits near-infrared light having a peak at the second wavelength, the photoelectric conversion device included in the first pixel has an absorption edge wavelength shorter than the second wavelength, and the photoelectric conversion device included in the second pixel has an absorption edge wavelength longer than or equal to the second wavelength.

A structure may be employed in which a first wavelength<a second wavelength, the light-emitting device included in the first pixel emits near-infrared light having a peak at the first wavelength, the light-emitting device included in the second pixel emits near-infrared light having a peak at the second wavelength, and the photoelectric conversion devices included in the first pixel and the second pixel have an absorption edge wavelength longer than or equal to the second wavelength. In that structure, the first pixel may be provided with a first optical filter layer selectively transmitting light with the first wavelength and a neighborhood thereof, and the second pixel may be provided with a second optical filter layer selectively transmitting light with the second wavelength and a neighborhood thereof.

The first pixel, the second pixel, the first correlated double sampling circuit, and the second correlated double sampling circuit may be provided between a first flexible substrate and a second flexible substrate facing the first flexible substrate.

It is preferable that the metal oxide include In, Zn, and M (M is Al, Tl, Ga, Ge, Sn, Y, Zr, La, Ce, Nd, or Hf).

Effect of the Invention

With one embodiment of the present invention, an imaging apparatus including a light source can be provided. An imaging apparatus that includes a thin light source and captures an image from light emitted from the light source and reflected by a subject can also be provided. An imaging apparatus including a thin infrared light source can also be provided. An imaging apparatus capable of product-sum operation of a plurality of pixels can also be provided.

An imaging apparatus with low power consumption can also be provided. An imaging apparatus capable of capturing an image at high speed can also be provided. An imaging apparatus with high reliability can also be provided. A novel-imaging apparatus can also be provided. A method for operating the above imaging apparatus can also be provided. A novel semiconductor device or the like can also be provided.

BRIEF DESCRIPTION OF THE DRAWINGS

FIG. 2A to FIG. 2C are diagrams each illustrating a pixel array.

FIG. 4A is a diagram showing a rolling shutter mode. FIG. 4B is a diagram showing a global shutter mode.

FIG. 17A1, FIG. 17A2, FIG. 17B1, and FIG. 17B2 are diagrams illustrating electronic devices.

MODE FOR CARRYING OUT THE INVENTION

Figure 1:
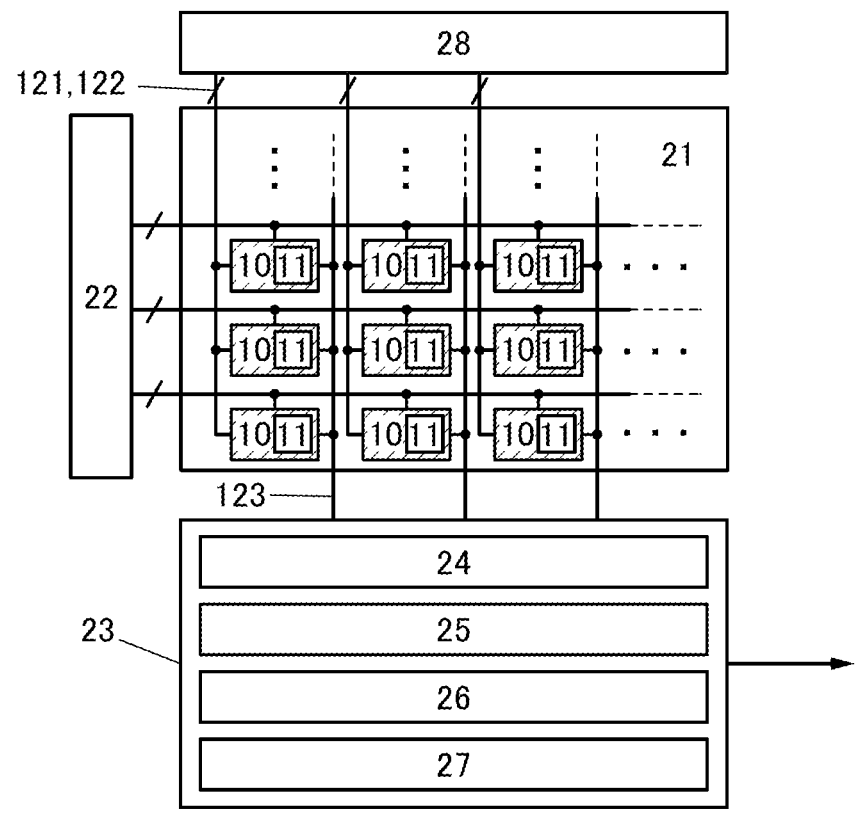
FIG. 1 is a block diagram illustrating an imaging apparatus.

Embodiments will be described in detail with reference to the drawings. However, the present invention is not limited to the following description, and it is readily appreciated by those skilled in the art that modes and details can be modified in various ways without departing from the spirit and the scope of the present invention. Thus, the present invention should not be interpreted as being limited to the description of embodiments below. Note that in structures of the invention described below, the same portions or portions having similar functions are denoted by the same reference numerals in different drawings, and the description thereof is not repeated in some cases. The same components may be denoted by different hatching patterns in different drawings, or the hatching patterns may be omitted in some cases.

Even in the case where a single component is illustrated in a circuit diagram, the component may be composed of a plurality of parts as long as there is no functional inconvenience. For example, in some cases, a plurality of transistors that operate as a switch may be connected in series or in parallel. In some cases, a capacitor (also referred to as a capacitive element) may be divided to be placed in a plurality of positions.

One conductor has a plurality of functions such as a wiring, an electrode, and a terminal in some cases. In this specification, a plurality of names may be used for the same component in some cases. Even in the case where components are illustrated in a circuit diagram as if they were directly connected to each other, the components may actually be connected to each other through a plurality of conductors; in this specification, even such a structure is included in direct connection.

Embodiment 1

In this embodiment, an imaging apparatus of one embodiment of the present invention is described with reference to drawings.

One embodiment of the present invention is an imaging apparatus including a light-emitting device and a photoelectric conversion device in a pixel. Light emitted from the light-emitting device and reflected by a subject is received by the photoelectric conversion device. Since an EL element is used as the light-emitting device, a thin imaging apparatus with a light source can be formed.

Furthermore, a structure in which a plurality of EL elements with different emission wavelengths are provided and a structure in which a plurality of photoelectric conversion devices with different light-receiving wavelengths are provided may also be employed. Thus, information of the subject with respect to a plurality of wavelengths can be obtained.

In addition, the imaging apparatus has a function of outputting third data generated by multiplying first data, which is obtained by the pixel, by second data (weight). Calculating the third data externally enables more detailed information of the subject with respect to a specific wavelength to be obtained. In addition, reading out collectively a plurality of pixels to which proper weight is given enables output of difference data between pixels and the like, which allows external calculation to be omitted.

When an element that emits infrared light is used as the light-emitting device, the imaging apparatus can be used for the purposes of biometric authentication, measurement of physical activity, failure analysis of industrial products, selection of farm products, and the like. When a pixel circuit that can take images with the global shutter mode is used, undistorted images can be taken even if the subject is moving.

<Imaging Apparatus>

FIG. 1 is a block diagram illustrating an imaging apparatus of one embodiment of the present invention. The imaging apparatus includes a pixel array 21 including pixels arranged in a matrix, a circuit 22 having a function of selecting a row of the pixel array 21 (row driver), a circuit 23 having a function of reading out data from the pixel circuits 10, and a circuit 28 which supplies a power supply potential. In the pixel, pixel circuits 10 and light-emitting devices 11 are provided.

The circuit 23 is a read circuit, and can include a circuit 24 (first CDS circuit) for performing correlated double sampling on output data of the pixel circuit 10, a circuit 25 (second CDS circuit) for performing correlated double sampling on output data of the circuit 24, a circuit 26 (A/D converter circuit or the like) having a function of converting analog data output from the circuit 25 to digital data, a circuit 27 (column driver) having a function of selecting a column of the pixel array 21 from which data is read out, and the like. A current supply circuit or the like can also be provided in the circuit 23.

Figures 2A, 2B, 2C:
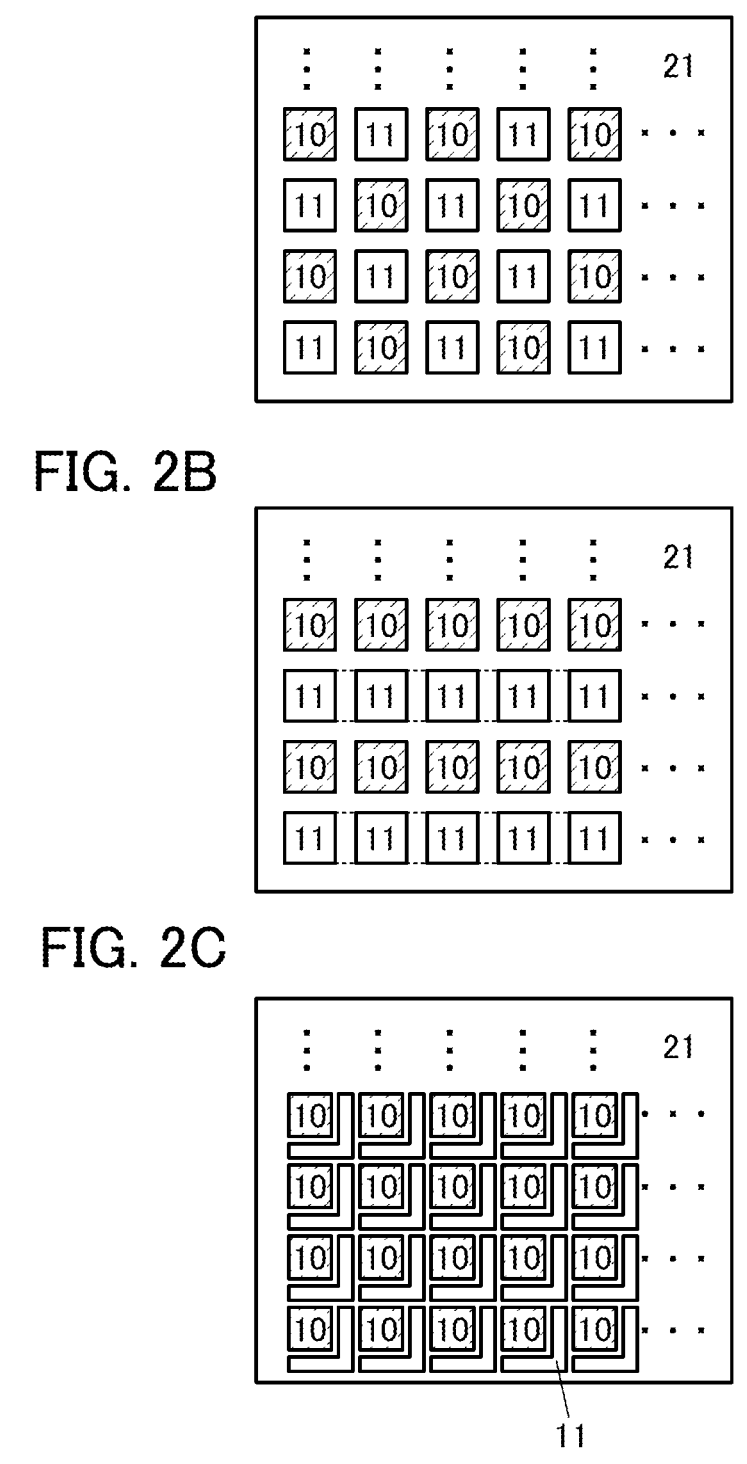

Note that a structure in which the pixel circuits 10 and the light-emitting devices 11 do not overlap with each other may be employed. For example, as illustrated in FIG. 2A, the pixel circuits 10 and the light-emitting devices 11 may be alternately arranged at regular intervals. As illustrated in FIG. 2B, the pixel circuits 10 and the light-emitting devices 11 may be alternately arranged row by row. As a modification example of the structure in FIG. 2B, a structure in which the light-emitting devices 11 are extended in one direction as indicated by dashed lines can be employed.

As illustrated in FIG. 2C, a structure in which the light-emitting device 11 is provided between two adjacent pixel circuits 10 may be employed. In this case, the light-emitting device 11 is provided so as to include a region overlapping with a wiring connected to the pixel circuit 10. Note that although the same number of light-emitting devices 11 as the number of pixel circuits 10 are illustrated in FIG. 2A to FIG. 2C, the number of light-emitting devices 11 may be different from that of pixel circuits 10.

<Pixel Circuit>

Figure 3:
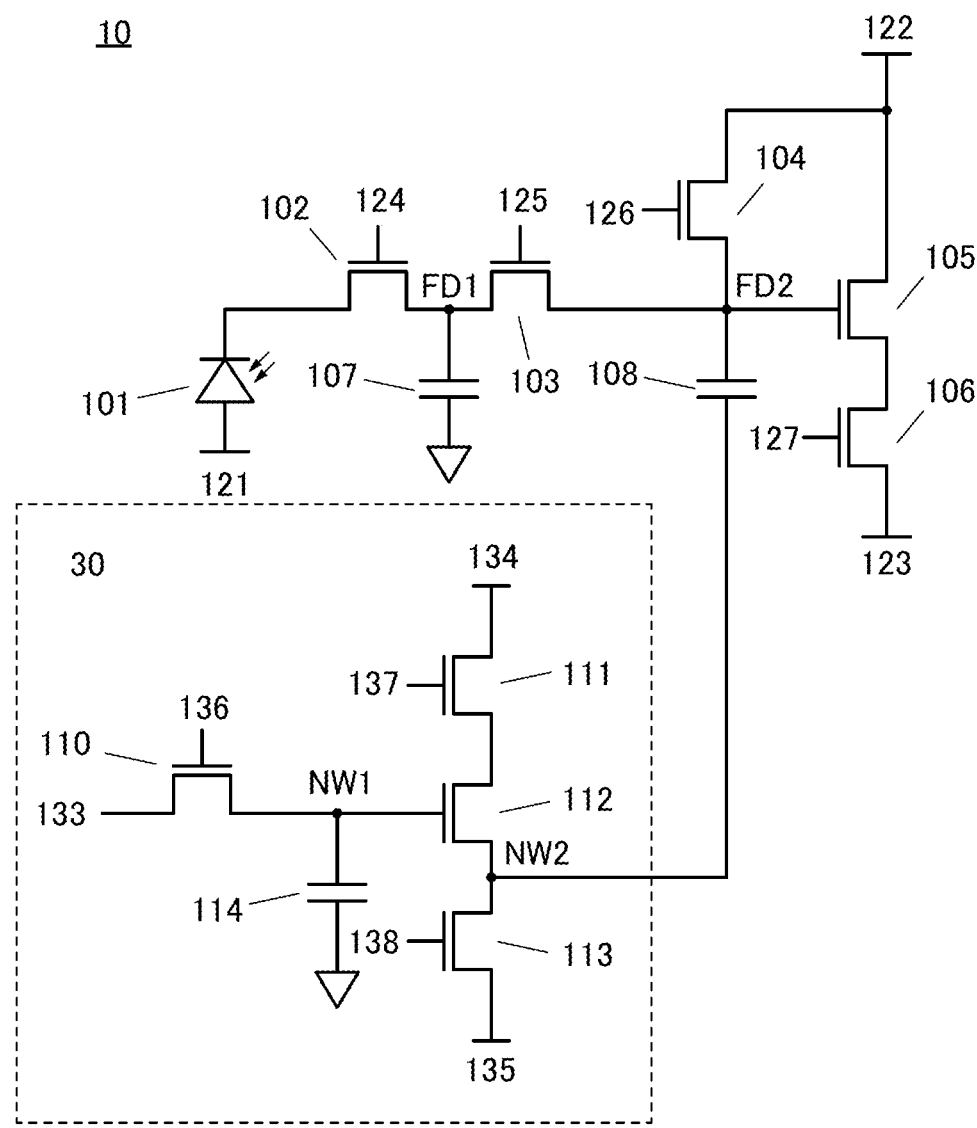
FIG. 3 is a diagram illustrating a pixel circuit.

FIG. 3 is a circuit diagram illustrating the pixel circuit 10 that can be used for an imaging apparatus of one embodiment of the present invention. The pixel circuit 10 can include a photoelectric conversion device 101, a transistor 102, a transistor 103, a transistor 104, a transistor 105, a transistor 106, a capacitor 107, a capacitor 108, and a memory circuit 30. Note that the capacitor 107 does not have to be provided.

One electrode (cathode) of the photoelectric conversion device 101 is electrically connected to one of a source and a drain of the transistor 102. The other of the source and the drain of the transistor 102 is electrically connected to one electrode of the capacitor 107. The one electrode of the capacitor 107 is electrically connected to one of a source and a drain of the transistor 103. The other of the source and the drain of the transistor 103 is electrically connected to one of a source and a drain of the transistor 104. The one of the source and the drain of the transistor 104 is electrically connected to one electrode of the capacitor 108. The one electrode of the capacitor 108 is electrically connected to a gate of the transistor 105. One of a source and a drain of the transistor 105 is electrically connected to one of a source and a drain of the transistor 106. The other electrode of the capacitor 108 is electrically connected to the memory circuit 30.

The memory circuit 30 includes a transistor 110, a transistor 111, a transistor 112, a transistor 113, and a capacitor 114.

One of a source and a drain of the transistor 110 is electrically connected to one electrode of the capacitor 114. The one electrode of the capacitor 114 is electrically connected to a gate of the transistor 112. One of a source and a drain of the transistor 112 is electrically connected to one of a source and a drain of the transistor 111. The other of the source and the drain of the transistor 112 is electrically connected to one of a source and a drain of the transistor 113. The one of the source and the drain of the transistor 113 is electrically connected to the other electrode of the capacitor 108.

Here, a wiring that connects the other of the source and the drain of the transistor 102, the one electrode of the capacitor 107, and the one of the source and the drain of the transistor 103 is a node FD1. A wiring that connects the other of the source and the drain of the transistor 103, the one of the source and the drain of the transistor 104, the one electrode of the capacitor 108, and the gate of the transistor 105 is a node FD2.

The node FD1 can function as a charge accumulation portion. The node FD2 can function as a charge detection portion.

In the memory circuit 30, a wiring that connects the one of the source and the drain of the transistor 110, the one electrode of the capacitor 114, and the gate of the transistor 112 is a node NW1. A wiring that connects the other of the source and the drain of the transistor 112, the one of the source and the drain of the transistor 113, and the other electrode of the capacitor 108 is a node NW2.

The node NW1 can function as a data storage node. The node NW2 can function as a data read node.

The other electrode (anode) of the photoelectric conversion device 101 is electrically connected to a wiring 121. A gate of the transistor 102 is electrically connected to a wiring 124. A gate of the transistor 103 is electrically connected to a wiring 125. The other of the source and the drain of the transistor 104 and the other of the source and the drain of the transistor 105 are electrically connected to a wiring 122. A gate of the transistor 104 is electrically connected to a wiring 126. A gate of the transistor 106 is electrically connected to a wiring 127. The other of the source and the drain of the transistor 106 is electrically connected to a wiring 123. The other electrode of the capacitor 107 is electrically connected to a reference potential line such as a GND wiring, for example.

In the memory circuit 30, the other of the source and the drain of the transistor 110 is electrically connected to a wiring 133. The other of the source and the drain of the transistor 111 is electrically connected to a wiring 134. The other of the source and the drain of the transistor 113 is electrically connected to a wiring 135. The other electrode of the capacitor 114 is electrically connected to a reference potential line such as a GND wiring, for example.

The wirings 124, 125, 126, 127, 136, 137, and 138 can function as signal lines that control the conduction of the respective transistors.

The wirings 121 and 122 can each have a function of a power supply line. The structure illustrated in FIG. 3 is a structure in which the cathode side of the photoelectric conversion device 101 is electrically connected to the transistor 102 and the node FD1 and the node FD2 are reset to a high potential in the operation; accordingly, the wiring 122 is set to a high potential (a potential higher than that of the wiring 121).

In the memory circuit 30, the transistor 112 and the transistor 113 each operate as a source follower to enable a potential of the node NW1 to be read out to the node NW2. The wiring 134 and the wiring 135 can each have a function of a power supply line for driving the transistor 112, and the wiring 134 is set to a high potential (a potential higher than that of the wiring 135).

The wiring 123 can function as an output line. The wiring 133 in the memory circuit can function as a signal line for data (weight) write.

As the photoelectric conversion device 101, a photodiode can be used. In one embodiment of the present invention, image capturing using infrared rays is performed. Thus, a photodiode that can at least convert light in the infrared region into electricity is used as the photoelectric conversion device 101.

A photodiode including an organic photoconductive film as a photoelectric conversion layer can be used, for example. An organic photoconductive film is a thin film, and can be bent in the case where a supporting substrate has flexibility. Thus, it is suitable for the formation of an imaging apparatus having flexibility. It also facilitates the increase in size of the imaging apparatus. Note that a photoconductor including an organic photoconductive film can also be used as the photoelectric conversion device 101.

In addition, a pn junction photodiode in which single crystal silicon is used in a photoelectric conversion portion, a pin photodiode in which polycrystalline silicon or microcrystalline silicon is used in a photoelectric conversion layer, or the like can also be used. Alternatively, a photodiode including a material capable of photoelectric conversion of infrared-region light, e.g., a compound semiconductor, may be used.

Note that many of the materials that can be used for the photodiodes or photoconductors also have sensitivity to a visible light region, enabling visible light images to be obtained. In the case where visible light serves as noise when an infrared light image is obtained, an infrared-ray transmitting filter (filter that blocks visible light) is preferably provided between the photoelectric conversion device 101 and the subject.

The transistor 102 has a function of controlling the potential of the node FD1. The transistor 103 has a function of controlling the potential of the node FD2. The transistor 104 has a function of resetting the potentials of the node FD1 and the node FD2. The transistor 105 functions as a source follower circuit, and can output the potential of the node FD2 as image data to the wiring 123. The transistor 106 has a function of selecting a pixel from which the image data is output.

Transistors using a metal oxide in their channel formation regions (hereinafter, OS transistors) are preferably used as the transistor 102, the transistor 103, and the transistor 104. An OS transistor has a feature of an extremely low off-state current. When OS transistors are used as the transistors 102, the transistor 103, and the transistor 104, a period during which charge can be retained at the node FD1 and the node FD2 can be elongated greatly. Thus, the global shutter mode, in which charge-accumulation operation is performed in all the pixels at the same time, can be used without complicating the circuit configuration and operation method.

<Operation Mode of Imaging Apparatus>

FIG. 4A is a schematic view of the operation method with the rolling shutter mode, and FIG. 4B is a schematic view of the global shutter mode. Note that En denotes exposure (accumulation operation) in the n-th column (n is a natural number), and Rn denotes reading operation in the n-th column. In FIG. 4A and FIG. 4B, operations from the first row (Line [1]) to the M-th row (Line [M]) (M is a natural number) are shown.

The rolling shutter mode is the operation method in which the exposure and data reading are performed sequentially and a reading period of a row overlaps with an exposure period of another row. The reading operation is performed right after the exposure; capturing images can be performed even with a circuit structure having a relatively short data-holding period. However, a one-frame image is composed of data that do not have simultaneity of image capturing; thus taking an image of a moving object leads to a distorted image.

In the global shutter mode, exposure is performed on all the pixels simultaneously, data is held in every pixel, and data reading is performed row by row. Thus, an image without distortion can be obtained even when an image of a moving object is captured.

In the case where a transistor having a relatively high off-state current, such as a transistor that uses Si in its channel formation region (hereinafter, Si transistor), is used in a pixel circuit, a data potential is likely to outflow from a charge accumulation portion; therefore, a rolling shutter method is used. The global shutter mode with Si transistors needs an additional memory circuit or the like, and complex operations must be rapidly performed. When an OS transistor is used in a pixel circuit, however, the data potential hardly leaks from the charge accumulation portion, which easily enables the global shutter mode.

It is preferable to use OS transistors as the transistor 110, the transistor 111, the transistor 112, and the transistor 113 in the memory circuit 30 as well. When an OS transistor is used as the transistor 110, the charge of the node NW1 can be retained for a very long period. Thus, with the same data, frequency with which the same data is written to the node NW1 can be decreased.

In addition, the use of OS transistors as the transistor 111, the transistor 112, and the transistor 113 can enable the potential of the node NW2 to be retained for a very long period. When the potential of the node NW2 can be retained for a long period, the potential of the node FD2 becomes stable, which enables reliable data to be read out from the pixel circuit 10.

Note that an OS transistor may also be used as the other transistor included in the pixel circuit 10. Alternatively, OS transistors and Si transistors may be freely used in combination. Alternatively, all the transistors may be OS transistors. Alternatively, all the transistors may be Si transistors. Examples of the Si transistor include a transistor containing amorphous silicon and a transistor containing crystalline silicon (typically, low-temperature polysilicon, single crystal silicon, or the like).

An EL element can be used as the light-emitting device 11. As the EL element, an element that emits infrared light can be used. In particular, the EL element preferably emits near-infrared light having a peak at a wavelength higher than or equal to 700 nm and lower than or equal to 2500 nm. For example, light having a wavelength of 760 nm and its vicinity is easily absorbed by reduced hemoglobin in the vein, so that the position of the vein can be detected by making an image from received reflected light or the like from a palm, a finger, or the like. This action can be utilized for biometric identification.

Furthermore, by comparing the amount of received light with a wavelength at which reduced hemoglobin exhibits high absorption and the amount of light with a wavelength (940 nm, for example) at which oxygenated hemoglobin exhibits high absorption, a region where neural activity of a living body is active can be detected. This function can be used for analysis of brain functions or the like. In a similar manner, by comparing the amount of received light with a wavelength at which reduced hemoglobin exhibits absorption and the amount of light with a wavelength at which oxygenated hemoglobin exhibits absorption, an oxygen concentration in the blood can be measured. Note that the blood sugar level can also be measured when the subject of absorption of infrared light is glucose.

In addition to the above, with the use of near-infrared light having an appropriate wavelength, non-destructive testing such as foreign body inspection of foods or failure analysis of industrial products can be performed. Furthermore, combination with a global shutter mode enables highly accurate sensing even while the target is moving.

For analysis of the brain functions, an imaging apparatus (sensor) with a relatively large area need to stick firmly to the head; thus, it is preferred that the imaging apparatus have flexibility or the imaging apparatus having flexibility be formed on a curved surface along the head shape. In order to render the imaging apparatus flexible, a method in which the imaging apparatus is first fabricated on a hard substrate and then transferred to a soft substrate is employed.

In that case, an organic resin such as polyimide is used as a buffer layer for separating the imaging apparatus from a hard substrate, so that the process temperature of the transistor or the like is restricted in some cases. Accordingly, the electrical characteristics and reliability of transistors may be degraded. In addition, formation of a transistor using polycrystalline silicon needs laser irradiation, which may cause separation defects due to the laser damage to the buffer layer and the peripheral members.

Thus, the use of OS transistors is preferable when an imaging apparatus having flexibility is fabricated. An OS transistor can be formed at relatively low temperatures and a laser irradiation process is not needed, so that the above problem does not occur. Thus, an OS transistor is suitable for an imaging apparatus having flexibility.

When an EL element is used as the light-emitting device 11, a thin imaging apparatus with a light source can be achieved. The imaging apparatus can easily be incorporated in various devices and the portability can be improved.

<Read Circuit>

Figure 5:
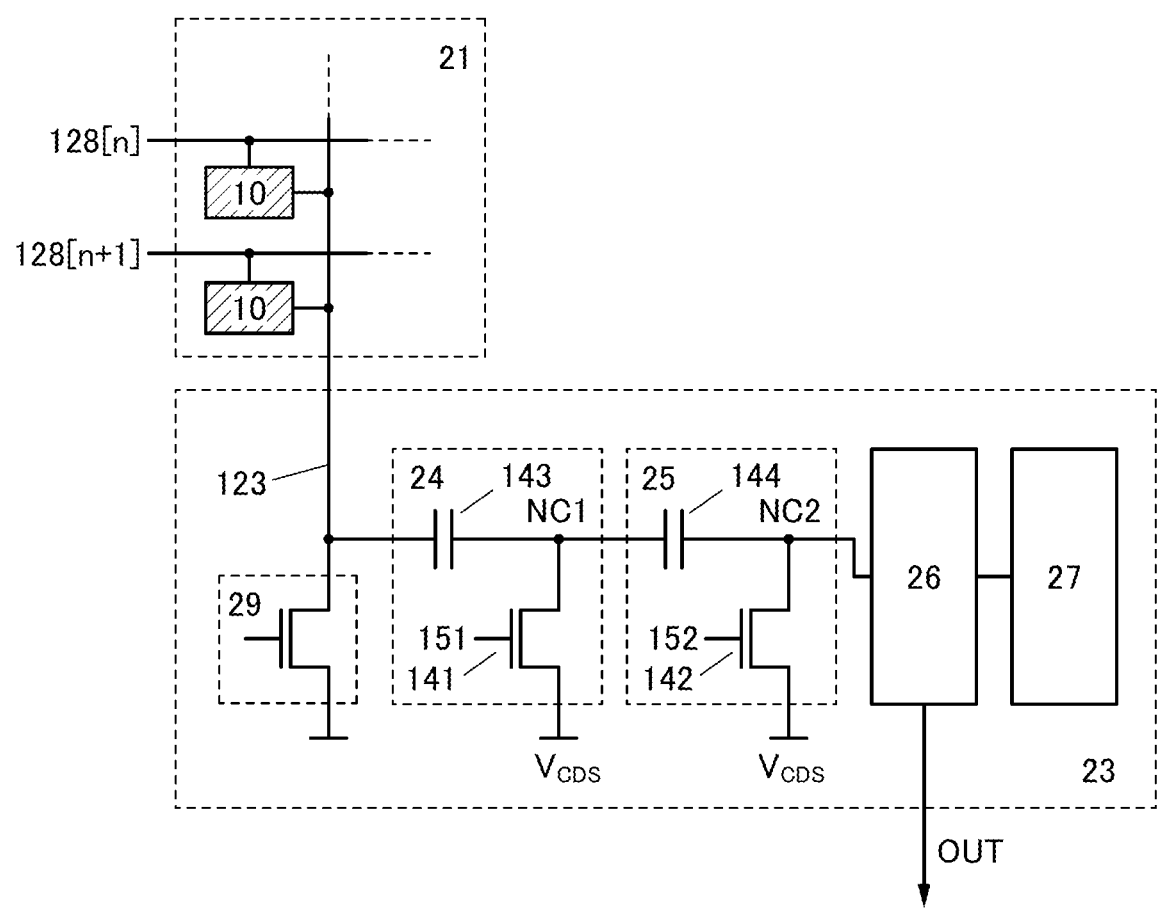
FIG. 5 is a circuit diagram illustrating a read circuit.

FIG. 5 is a diagram illustrating the circuit 23 that is connected to a certain column of the pixel array 21. A current source circuit 29 is electrically connected to the wiring 123 through which data is output from the pixel circuit 10. In addition, the circuit 24 (first CDS circuit), the circuit 25 (second CDS circuit), the circuit 26 (A/D converter circuit), and the circuit 27 (shift register) are sequentially connected to the wiring 123.

The circuit 24 can have a structure including a transistor 141 and a capacitor 143. The circuit 25 can have a structure including a transistor 142 and a capacitor 144.

One electrode of the capacitor 143 is electrically connected to the wiring 123. The other electrode of the capacitor 143 is electrically connected to one of a source and a drain of the transistor 141. The one of the source and the drain of the transistor 141 is electrically connected to one electrode of the capacitor 144. The other electrode of the capacitor 144 is electrically connected to one of a source and a drain of the transistor 142. The one of the source and the drain of the transistor 142 is electrically connected to the circuit 26. The circuit 26 is electrically connected to the circuit 27. The circuit 26 can include a comparator, a counter, and an output unit (OUT), for example.

Here, a wiring that connects the other electrode of the capacitor 143, the one of the source and the drain of the transistor 141, and the one electrode of the capacitor 144 is a node NC1. A wiring that connects the other electrode of the capacitor 144, the one of the source and the drain of the transistor 142, and the circuit 26 is a node NC2.

The other of the source and the drain of the transistor 141 and the other of the source and the drain of the transistor 142 are electrically connected to a wiring capable of supplying a reference potential ($V_{CDS}$)

<Output Data of Imaging Apparatus>

The imaging apparatus of one embodiment of the present invention is capable of outputting third data generated by multiplying first data, which is obtained by the pixel, by second data (weight). The third data can be generated using the pixel circuit 10, the circuit 24, and the circuit 25, and unnecessary components are removed. The description thereon is as follows.

The third data is generated using data without exposure ($D_r$), data without exposure to which weight is added ($D_{r+w}$), data with exposure ($D_{r+x}$), and data with exposure to which weight is added ($D_{r+x+w}$), which are output from the pixel circuit 10.

When the pixel circuit 10 outputs $D_r$, a current that is proportional to a function of Formula (1) flows in the wiring 123. Here, r represents a reset potential, $V_{th}$ represents the threshold voltage of the transistor 105, and r corresponds to the potential of the node FD2 during read.

$$(r-V_{th})^2 \quad (1)$$

When the pixel circuit 10 outputs $D_{r+w}$, a current that is proportional to a function of Formula (2) flows in the wiring 123. Here, w represents weight, and r+w corresponds to the potential of the node FD2 during read.

$$(r+w-V_{th})^2 \quad (2)$$

When the pixel circuit 10 outputs $D_{r+x}$, a current that is proportional to a function of Formula (3) flows in the wiring 123. Here, x represents the amount of change in potential due to exposure, and r+x corresponds to the potential of the node FD2 during read.

$$(r+x-V_{th})^2 \quad (3)$$

When the pixel circuit 10 outputs $D_{r+x+w}$, a current that is proportional to a function of Formula (4) flows in the wiring 123. Here, r+x+w corresponds to the potential of the node FD2 during read.

$$(r+x+w-V_{th})^2 \quad (4)$$

Here, the amount of change (difference) between with and without weight is calculated in each of the cases, i.e., with and without exposure. Specifically, Formula (2)–Formula (1), and Formula (4)–Formula (3) are calculated.

$$(r+w-V_{th})^2-(r-V_{th})^2=w(2r+w-2V_{th}) \quad (5)$$

$$(r+x+w-V_{th})^2-(r+x-V_{th})^2=w(2r+2x+w-2V_{th}) \quad (6)$$

When Formula (6)–Formula (5) is further calculated, a solution is found to be 2wx as shown in Formula (7).

$$w(2r+2x+w-2V_{th})-w(2r+w-2V_{th})=2wx \quad (7)$$

That is, information related to the product of the exposure data (x) and the weight (w) can be extracted. The operations for outputting data corresponding to Formulae (1) to (4) above can be performed in the pixel circuit 10. The calculation operations of data corresponding to Formula (5) and Formula (6) can be mainly performed in the circuit 24. The calculation operation of data corresponding to Formula (7) can be mainly performed in the circuit 25.

<Operation of Imaging Apparatus>

Next, a specific operation example of the pixel circuit 10, the circuit 24, and the circuit 25 will be described with reference to a timing chart in FIG. 6. Note that in the description of the timing chart in this specification, a high potential is denoted by "H" and a low potential is denoted by "L". The wirings 121, 123, and 135 are always supplied with "L", and the wirings 122 and 134 are always supplied with "H".

Note that although the operation of the light-emitting device 11 is not mentioned here, the light-emitting device 11 is in a state of being supplied with a power supply potential for appropriately causing light emission at least in an accumulation operation period.

In period T1, the potential of the wiring 124 is set to "H", the potential of the wiring 125 is set to "H", the potential of the wiring 126 is set to "H", the potential of the wiring 127 is set to "L", the potential of the wiring 136 is set to "H", the potential of the wiring 137 is set to "L", the potential of the wiring 138 is set to "H", the potential of the wiring 151 is set to "L", and the potential of the wiring 152 is set to "L", whereby the transistors 102, 103, and 104 are turned on and the potential "H" (r: reset potential) of the wiring 122 is supplied to the node FD1 and the node FD2 (reset operation).

In the memory circuit 30, the transistor 113 is turned on, and the potential "L" of the wiring 135 is written to the node NW2. At this time, "r–L" is retained in the capacitor 108. Furthermore, the transistor 110 is turned on, and the potential "w" supplied from the wiring 133 is written to the node NW1. Note that write of weight to the node NW1 does not necessarily need to be performed in period T1 but is performed before the weight is read out to the node NW2.

In period T2, the potential of the wiring 124 is set to "H", the potential of the wiring 125 is set to "L", the potential of the wiring 126 is set to "L", the potential of the wiring 127 is set to "L", the potential of the wiring 136 is set to "L", the potential of the wiring 137 is set to "L", the potential of the wiring 138 is set to "H", the potential of the wiring 151 is set to "L", and the potential of the wiring 152 is set to "L", whereby the transistors 103 and 104 are turned off and the reset potential "r" is retained at the node FD2. The potential of the node FD1 is changed by the potential "x" of an exposure amount in accordance with the operation of the photoelectric conversion device 101 to be "r+x" (accumulation operation).

In period T3, the potential of the wiring 124 is set to "L", the potential of the wiring 125 is set to "L", the potential of the wiring 126 is set to "L", the potential of the wiring 127 is set to "L", the potential of the wiring 136 is set to "L", the potential of the wiring 137 is set to "L", the potential of the wiring 138 is set to "H", the potential of the wiring 151 is set to "L", and the potential of the wiring 152 is set to "L", whereby the transistor 102 is turned off and the potential of the node FD1 is fixed and retained. In addition, the transistor 110 is turned off and the potential of the node NW1 is retained.

In this case, the use of OS transistors with low off-state current as the transistor 102, the transistor 103, the transistor 104, and the transistor 110 can suppress unnecessary flow of charge from the node FD1, the node FD2, and the node NW1, whereby the retention period of each data can be extended.

In period T4, the potential of the wiring 124 is set to "L", the potential of the wiring 125 is set to "L", the potential of the wiring 126 is set to "L", the potential of the wiring 127 is set to "H", the potential of the wiring 136 is set to "L", the potential of the wiring 137 is set to "L", the potential of the wiring 138 is set to "H", the potential of the wiring 151 is set to "H", and the potential of the wiring 152 is set to "H", whereby the transistor 106 is turned on and current that is proportional to the function including the potential "r" of the node FD2, i.e., $(r-V_{th})^2$, flows in the wiring 123 (read operation 1) by the source follower operation of the transistor 105. The operation corresponds to Formula (1) mentioned above.

In addition, the transistor 141 in the circuit 24 and the transistor 142 in the circuit 25 are turned on, and the reference potential "$V_{CDS}$" is written to each of the node NC1 and the node NC2.

In period T5, the potential of the wiring 124 is set to "L", the potential of the wiring 125 is set to "L", the potential of the wiring 126 is set to "L", the potential of the wiring 127 is set to "H", the potential of the wiring 136 is set to "L", the potential of the wiring 137 is set to "H", the potential of the wiring 138 is set to "L", the potential of the wiring 151 is set to "L", and the potential of the wiring 152 is set to "H", whereby the transistor 111 is turned on and the transistor 113 is turned off, and the potential "w" of the node NW1 is read out to the node NW2 by the source follower operation of the transistor 112, in the memory circuit 30.

At this time, the potential of the node FD2 becomes "r−L+w" because of capacitive coupling of the capacitor 108. Here, when "L"=0 V, the potential of the node FD2 is "r+w". Thus, current that is proportional to the function $(r+w-V_{th})^2$ including "r+w" flows in the wiring 123 by the source follower operation of the transistor 105. The operation corresponds to Formula (2) mentioned above.

In the circuit 24, the transistor 141 is turned off. At this time, when "$V_{CDS}$"=0 V, the potential of the node NC1 becomes $(r+w-V_{th})^2-(r-V_{th})^2=w(2r+w-2V_{th})$ because of capacitive coupling of the capacitor 143. The operation corresponds to Formula (5) mentioned above.

In period T6, the potential of the wiring 124 is set to "L", the potential of the wiring 125 is set to "H", the potential of the wiring 126 is set to "L", the potential of the wiring 127 is set to "H", the potential of the wiring 136 is set to "L", the potential of the wiring 137 is set to "L", the potential of the wiring 138 is set to "H", and the potential of the wiring 151 is set to "H", and the potential of the wiring 152 is set to "L", whereby the transistor 103 is turned on and the potential "r+x" of the node FD1 is read out to the node FD2. Thus, current that is proportional to the function $(r+x-V_{th})^2$ including "r+w" flows in the wiring 123 by the source follower operation of the transistor 105. The operation corresponds to Formula (3) mentioned above.

In the memory circuit 30, the transistor 111 is turned off and the transistor 113 is turned on, whereby the potential "L" of the wiring 135 is written to the node NW2. At this time, "r+x−L" is retained in the capacitor 108.

In addition, the transistor 141 in the circuit 24 is turned on, and the reference potential "$V_{CDS}$" is written to the node NC1. The transistor 142 in the circuit 25 is turned off. Thus, the potential of the node NC2 becomes "$V_{CDS}-w(2r+w-2V_{th})$" because of capacitive coupling of the capacitor 144. In other words, when "$V_{CDS}$"=0 V, the potential of the node NC2 is "$-w(2r+w-2V_{th})$".

In period T7, the potential of the wiring 124 is set to "L", the potential of the wiring 125 is set to "H", the potential of the wiring 126 is set to "L", the potential of the wiring 127 is set to "H", the potential of the wiring 136 is set to "L", the potential of the wiring 137 is set to "H", the potential of the wiring 138 is set to "L", the potential of the wiring 151 is set to "L", and the potential of the wiring 152 is set to "L", whereby the transistor 111 is turned on and the transistor 113 is turned of, and the potential "w" of the node NW1 is read out to the node NW2 by the source follower operation of the transistor 112 in the memory circuit 30.

At this time, the potential of the node FD2 becomes "r+w−L+w" because of capacitive coupling of the capacitor 108. Here, when "L"=0 V, the potential of the node FD2 is "r+x+w". Thus, current that is proportional to the function $(r+x+w-V_{th})^2$ including "r+x+w" flows in the wiring 123 by the source follower operation of the transistor 105. The operation corresponds to Formula (4) mentioned above.

In the circuit 24, the transistor 141 is turned off. At this time, when "$V_{CDS}$"=0 V, the potential of the node NC1 becomes $(r+x+w-V_{th})^2-(r+x-V_{th})^2=w(2r+2x+w-2V_{th})$ because of capacitive coupling of the capacitor 143. The operation corresponds to Formula (6) mentioned above.

The transistor 142 in the circuit 25 is turned off. At this time, when "$V_{CDS}$"=0 V, the potential of the node NC2 becomes $w(2r+2x+w-2V_{th})-w(2r+w-2V_{th})=2wx$ because of capacitive coupling of the capacitor 144. The operation corresponds to Formula (7) mentioned above. Thus, information related to the product of the exposure data (x) and weight (w) can be extracted from the circuit 25.

The above is a specific operation example of the pixel circuit 10, the circuit 24, and the circuit 25.

<Modification Example of Imaging Apparatus>

Figure 7:
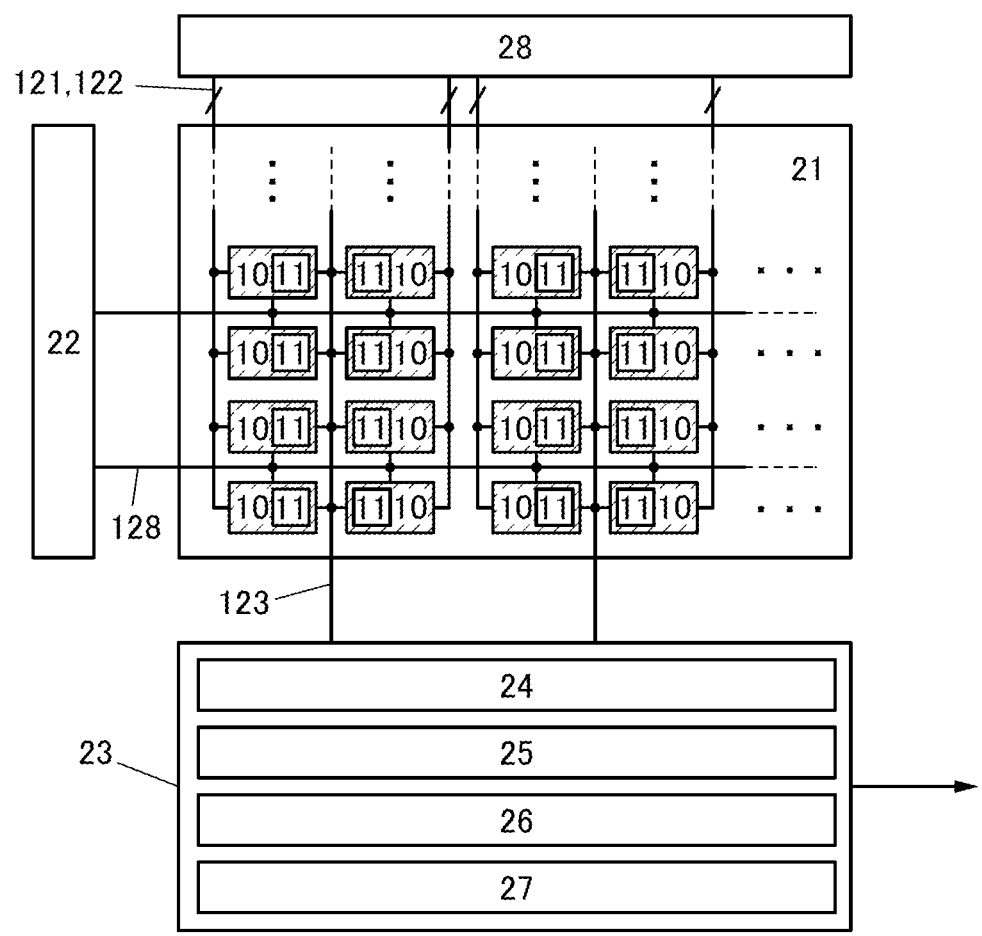
FIG. 7 is a block diagram illustrating an imaging apparatus.

The imaging apparatus of one embodiment of the present invention may have a structure of the block diagram shown in FIG. 7. The imaging apparatus shown in FIG. 7 differs from the imaging apparatus in FIG. 1 in that a read gate line (wiring 128) and an output line (wiring 123) are shared by a plurality of pixel circuits 10. Although FIG. 7 illustrates an example in which wirings such as output lines are shared by four pixels, the number of pixels is not limited as long as it is two or greater by which the total number of pixels can be equally divided.

With this structure, information on the product of the exposure data (x) and weight (w) obtained from a plurality of pixels can be collectively read out. In other words, product-sum operation using a plurality of pixels can be performed. Each of the plurality of pixels can output data multiplied by given weight. Thus, by multiplying data of some of the plurality of pixels by weight having a reversed sign, difference from the other pixels can be obtained without extracting the data outside.

Figure 6:
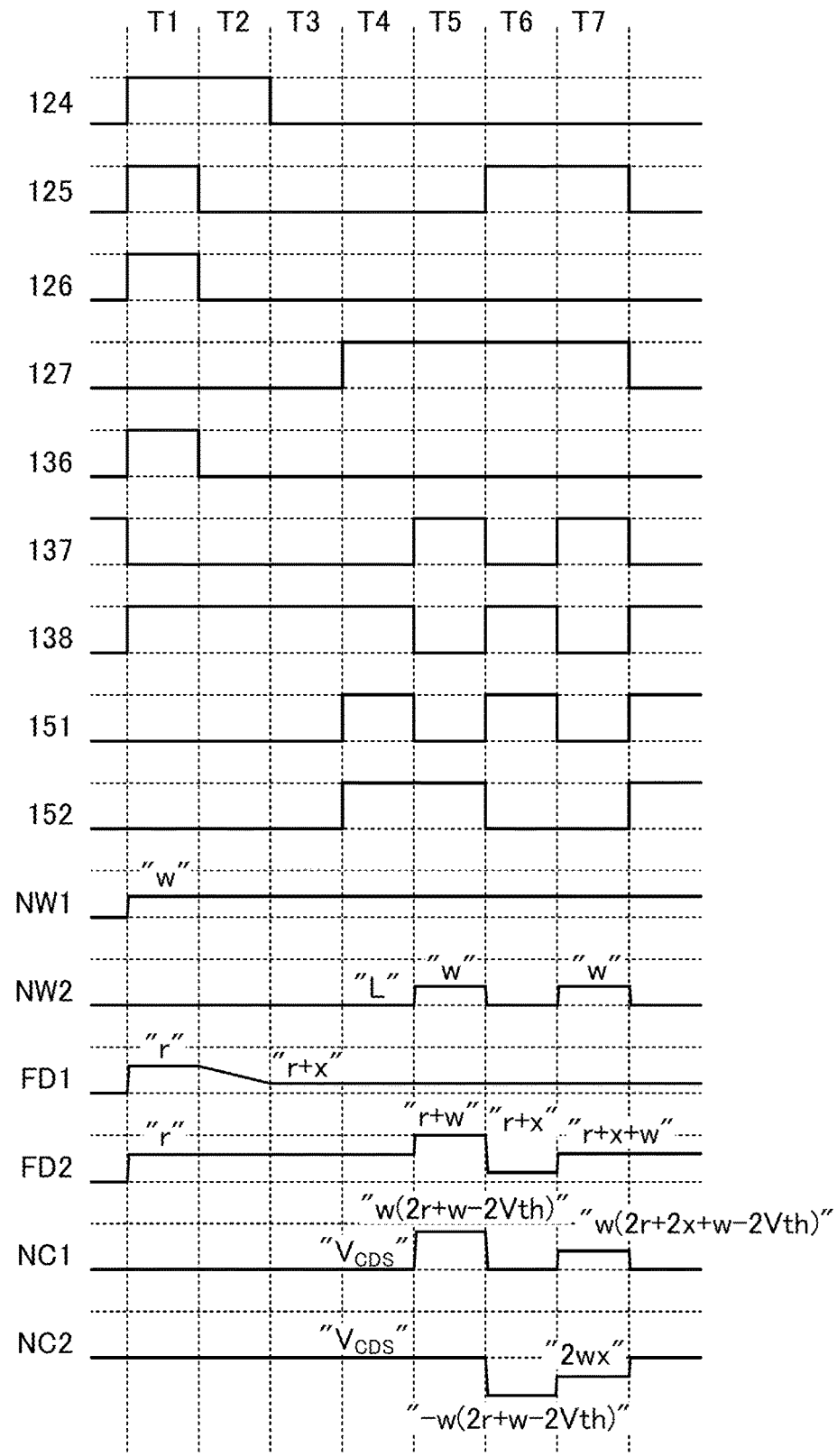
FIG. 6 is a timing chart showing the operation of an imaging apparatus.

The imaging apparatus can operate in accordance with the timing chart shown in FIG. 6 and its description. Derived functions will be shown below. Note that in the case where the number of pixels subjected to collective read-out is four, n is an integer of 1 to 4.

Current read out to the wiring 123 at time T4 is proportional to $\Sigma_n (r-V_{th})^2$.

Current read out to the wiring 123 at time T5 is proportional to $\Sigma_n (r+w_n-V_{th})^2$.

Current read out to the wiring 123 at time T6 is proportional to $\Sigma_n (r+x_n-V_{th})^2$. Current read out to the wiring 123 at time T7 is proportional to $\Sigma_n (r+x_n+w_n-V_{th})^2$.

Then, at the end of time T7, $\Sigma_n (x_n+w_n)$ can be obtained in the circuit 25.

<Light-Emitting Device and Imaging Device>

Figure 8A:
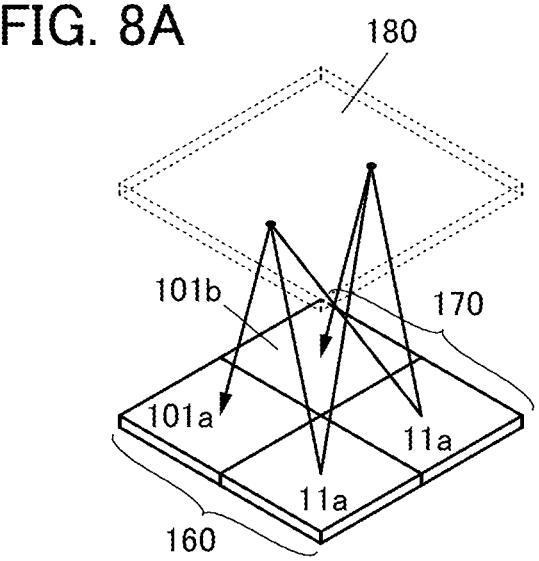
FIG. 8A to FIG. 8C are diagrams each illustrating a light-emitting device and a photoelectric conversion device.
Figure 8B:
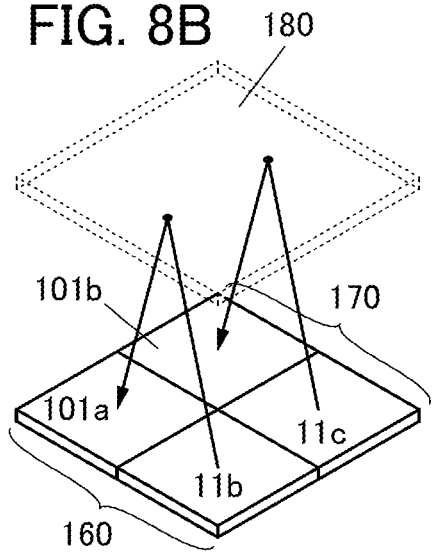
Figure 8C:
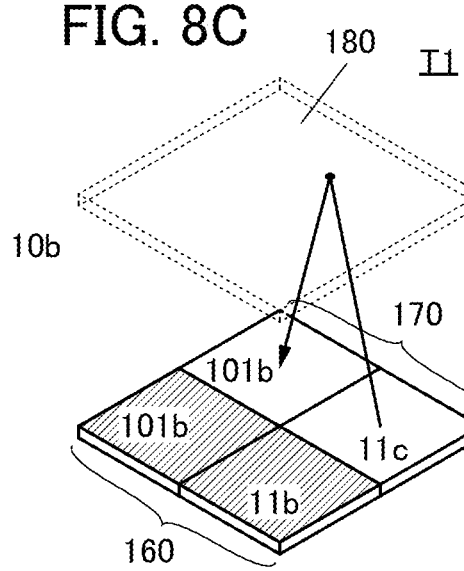

Next, combination of a light-emitting device and a photoelectric conversion device that can be included in each pixel will be described. FIG. 8A to FIG. 8C illustrate a first pixel 160, a second pixel 170, and a subject 180. The first pixel 160 and the second pixel 170 can be used as pixels in the pixel array 21. Note that the size of one side of each pixel, when it is regarded as a square, is less than or equal to 1 mm, preferably less than or equal to 100 μm.

FIG. 8A illustrates a structure in which the first pixel 160 includes a photoelectric conversion device 101a, the second pixel 170 includes a photoelectric conversion device 101b, and each of the pixels includes the light-emitting device 11a. Part of light emitted from the light-emitting device 11a is absorbed by the subject 180, and light reflected by the subject 180 is received by each pixel. Note that arrows in the drawings each indicate part of a light path.

In the case where the center wavelengths that are the objects of image capturing are two wavelengths, i.e., a wavelength A and a wavelength B (wavelength A<wavelength B), an EL element that emits light with a broad wavelength distribution including the wavelength A and the wavelength B can be used as the light-emitting device 11a. Here, the absorption edge wavelength of the photoelectric conversion device 101a can be shorter than the wavelength B, and the absorption edge wavelength of the photoelectric conversion device 101b can be longer than or equal to the wavelength B.

As the photoelectric conversion device 101a, a photodiode in which a semiconductor material with an absorption edge wavelength in the neighborhood of the wavelength A is used for a photoelectric conversion layer can be used. As the photoelectric conversion device 101b, a photodiode in which a semiconductor material with an absorption edge wavelength in the neighborhood of the wavelength B is used for a photoelectric conversion layer can be used.

Alternatively, the photoelectric conversion layer in each of the photoelectric conversion devices 101a and 101b may be formed of a semiconductor material having a sensitivity to a wavelength range including the wavelength A and the wavelength B. In that case, an optical filter that transmits the wavelength A and the neighborhood thereof is provided over the photoelectric conversion device 101a, and an optical filter that transmits the wavelength B and the neighborhood thereof is provided over the photoelectric conversion device 101b.

Such combination enables the first pixel 160 to obtain information on light with wavelengths in the neighborhood of the wavelength A and shorter than that. Such combination enables the second pixel 170 to obtain information on light with wavelengths in the neighborhood of the wavelength B and shorter than that. In other words, when difference between the information obtained by the second pixel 170 and the information obtained by the first pixel 160 is obtained, the data of the wavelength B and the neighborhood thereof can be extracted.

The use of the imaging apparatus shown in FIG. 1 enables output of image data obtained by each of the pixels and multiplied by weight. Thus, by extracting the data outside and performing differential calculation, only information on the wavelength B and the neighborhood thereof can be obtained.

In addition, when the imaging apparatus shown in FIG. 7 is used, pixels used for differential calculation are supplied with appropriate weight and the data is collectively read out, whereby only information on the wavelength B and the neighborhood thereof can be obtained.

Although two wavelengths of light are used in the above-described example, more than two wavelengths of light may be used.

FIG. 8B illustrates a structure in which the first pixel 160 includes the photoelectric conversion device 101a and the light-emitting device 11b, and the second pixel 170 includes the photoelectric conversion device 101b and the light-emitting device 11b. An EL element that emits light with a peak at the wavelength A can be used as the light-emitting device 11b. An EL element that emits light with a peak at the wavelength B can be used as a light-emitting device 11c.

In the structure shown in FIG. 8B, the wavelength distribution of the light source is not broad, so information on light with a peak at the wavelength A can be directly obtained by the photoelectric conversion device 101a. Information on light with a peak at the wavelength B can be directly obtained by the photoelectric conversion device 101b.

FIG. 8C illustrates a structure in which the first pixel 160 includes the light-emitting device 11b, the second pixel 170 includes the light-emitting device 11c, and each of the pixels includes the photoelectric conversion device 101b. With the absorption edge wavelength of the photoelectric conversion device 101b set at the wavelength B or longer, the first pixel 160 and the second pixel 170 are operated at different times (T1 and T2). This operation enables information on light with a peak at the wavelength B to be directly obtained by the photoelectric conversion device 101b in the pixel 170 at T1. At T2, information on light with a peak at the wavelength A can be directly obtained by the photoelectric conversion device 101b in the pixel 160.

Note that in the structures shown in FIG. 8B and FIG. 8C, differential calculation need not necessarily be performed; however, performing differential calculation can cut a noise component of unnecessary wavelengths in some cases.

<Modification Example of Pixel>

Figure 9A:
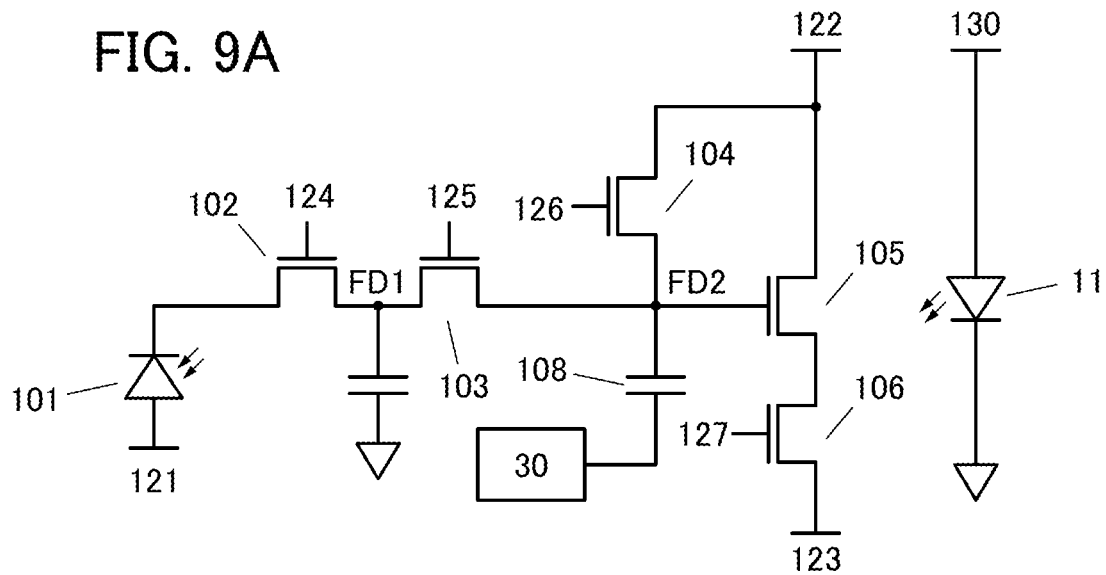
FIG. 9A to FIG. 9C are diagrams each illustrating a pixel circuit.

FIG. 9A is a circuit diagram illustrating the pixel circuit 10 and the light-emitting device 11 that can be provided in the imaging apparatus of one embodiment of the present invention. The pixel circuit 10 has the same configuration as that shown in FIG. 3.

Since the pixel circuit 10 and the light-emitting device 11 are not electrically connected in this pixel, the input potential to the light-emitting device 11 and the timing of light emission can be controlled independently. One electrode of the light-emitting device 11 is electrically connected to a wiring 130. The wiring 130 has a function of supplying a potential for supplying a forward bias to the light-emitting device 11 and causing light emission. The other electrode of the light-emitting device 11 is electrically connected to a reference potential line such as a GND wiring, for example.

Figure 9B:
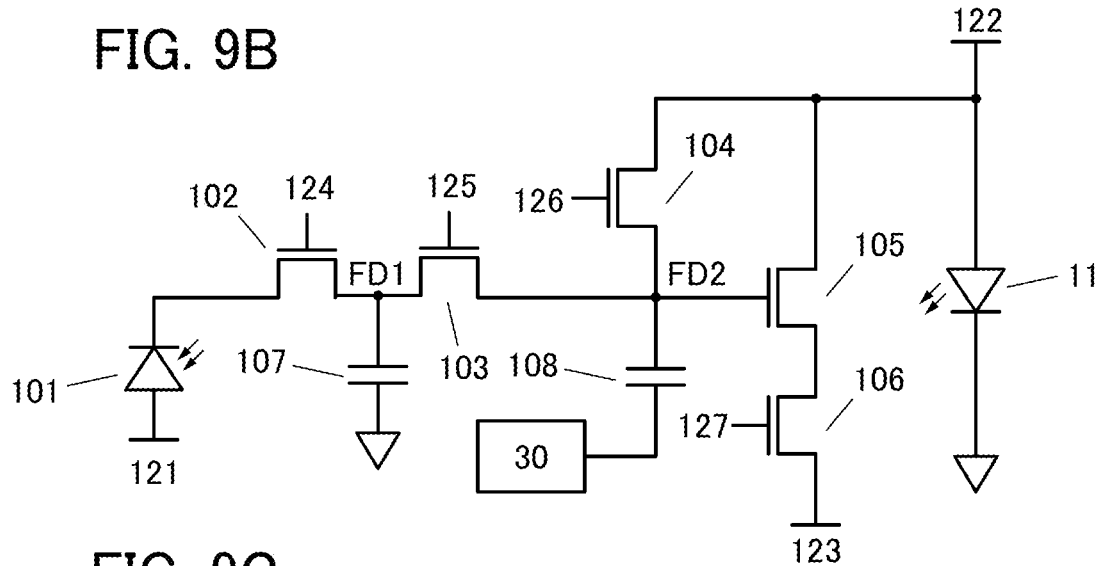

FIG. 9B illustrates a configuration in which the one electrode of the light-emitting device 11 is electrically connected to the wiring 122. This configuration can be employed in the case where a common potential can be used as the reset potential of the node FD1 and the node FD2, the power supply potential supplied to the transistor 105, and the input potential to the light-emitting device 11.

Figure 9C:
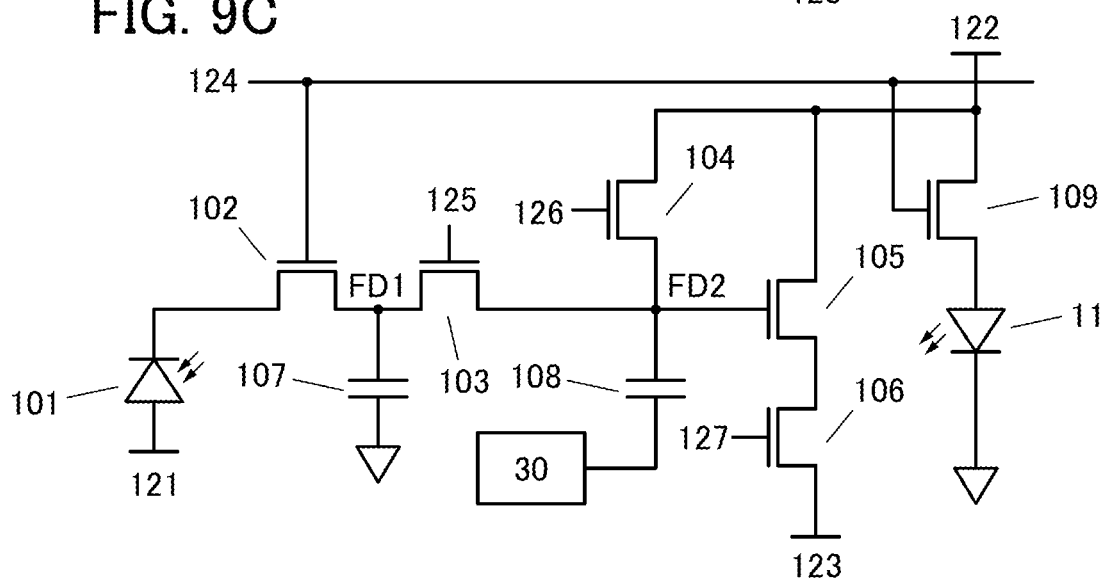

As illustrated in FIG. 9C, a transistor 109 may be added to the configuration of FIG. 9B. One of a source and a drain of the transistor 109 is electrically connected to the one electrode of the light-emitting device 11. The other of the source and the drain of the transistor 109 is electrically connected to the wiring 122. A gate of the transistor 109 is electrically connected to the wiring 124. With this configuration, the light emission period can be limited to only a period during which the transistor 102 is on, whereby the power consumption can be reduced. Since the transistor 102 needs to be on only in a reset operation period and an accumulation operation period for the node FD1, nonessential light emission in a read operation period or the like can be suppressed.

Figure 10A:
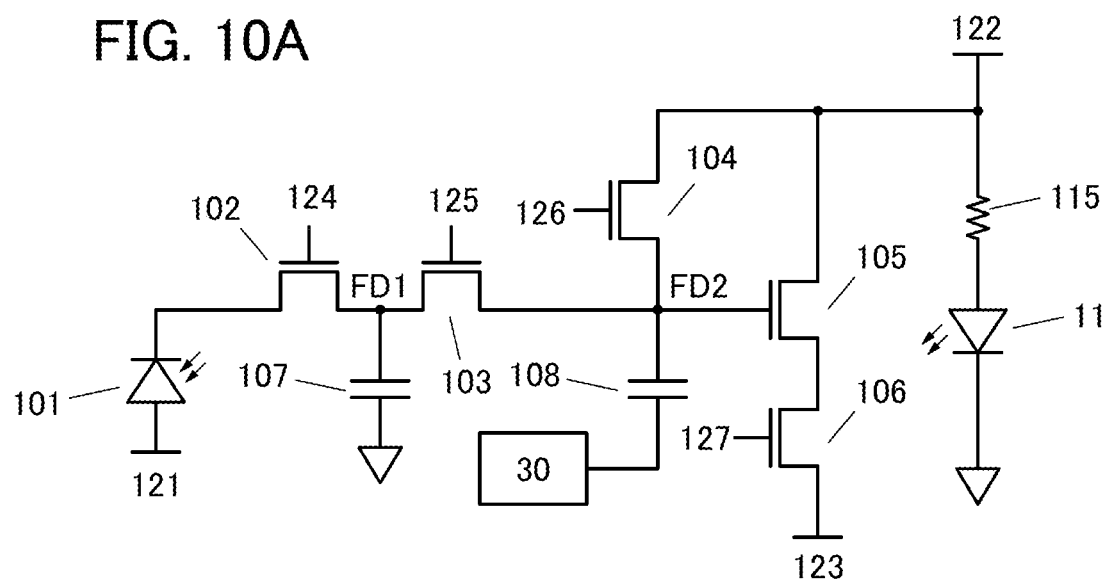
FIG. 10A to FIG. 10C are diagrams each illustrating a pixel circuit.

Furthermore, in the case where the reset potential of the node FD1 and the node FD2 is too high compared with an appropriate potential input to the light-emitting device 11, a resistor 115 may be electrically connected between the one electrode of the light-emitting device 11 and the wiring 122 as illustrated in FIG. 10A. The resistor 115 operates as a current-limiting resistance; limiting the current flowing through the light-emitting device 11 can enhance the reliability of the light-emitting device 11. The resistance value of the resistor 115 may be selected so as to be suitable for electrical characteristics of the light-emitting device 11.

Figure 10B:
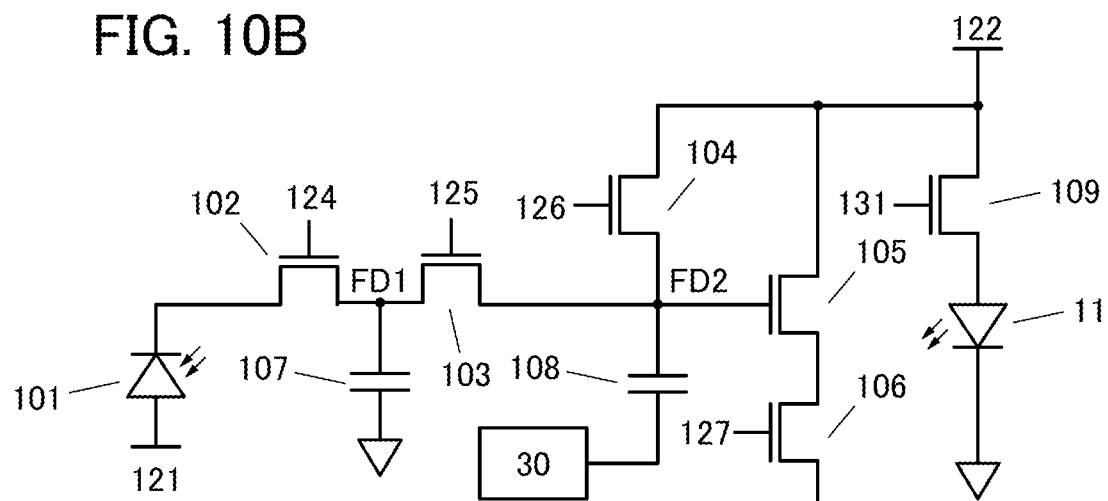

Note that as illustrated in FIG. 10B, the transistor 109 illustrated in FIG. 9C may operate as a substitute for the resistor 115. In this configuration, the gate of the transistor 109 is electrically connected to a wiring 131. Thus, changing the potential of the wiring 131 allows appropriate control of the illuminance of the light-emitting device 11 and the timing of light emission, so that power consumption can be suppressed.

Figure 10C:
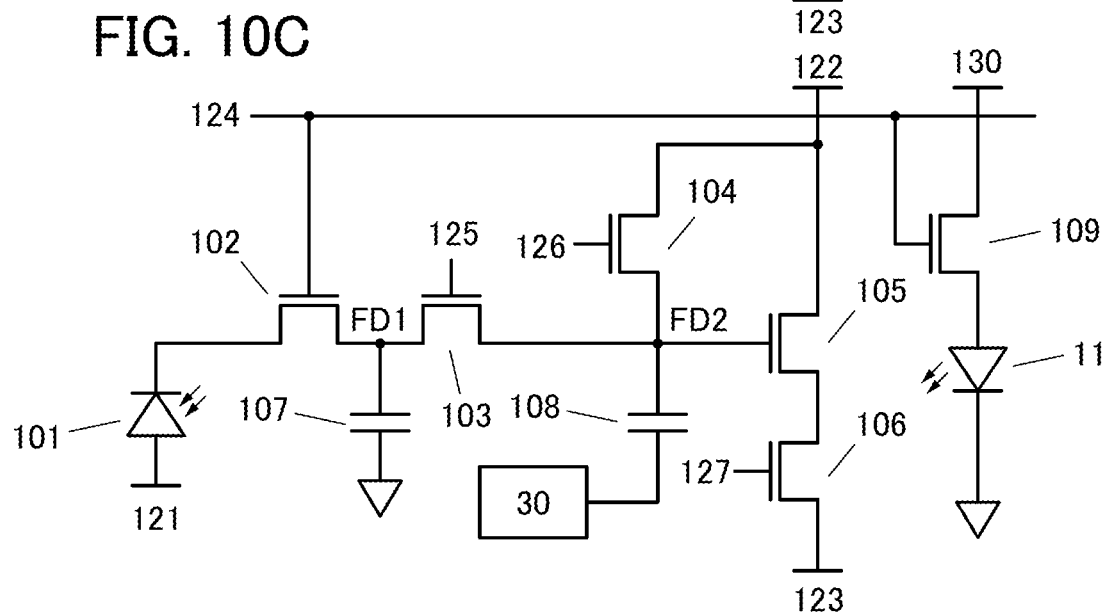
Figure 11A:
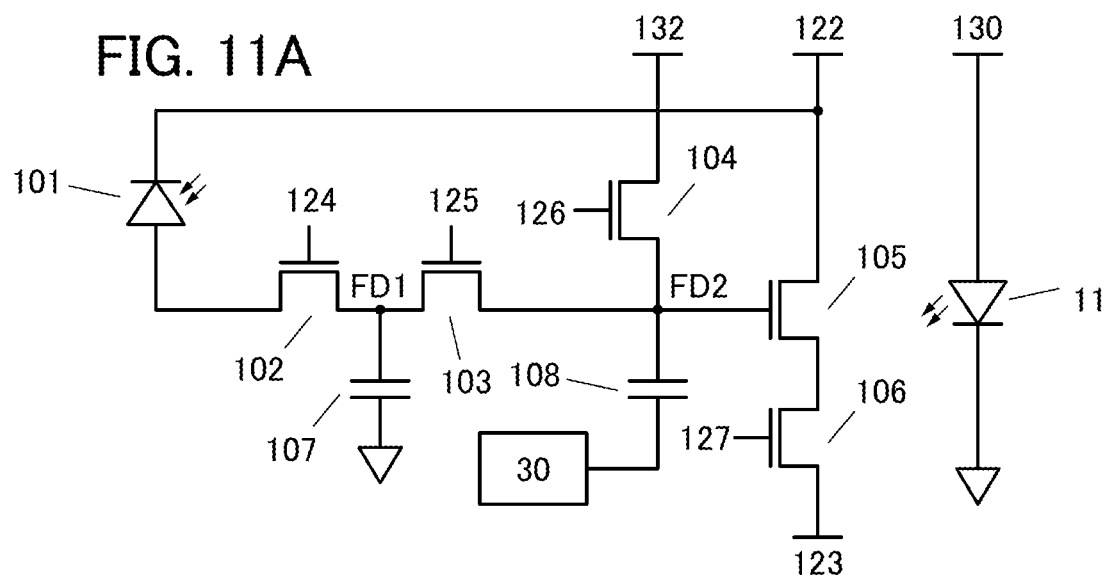
FIG. 11A to FIG. 11C are diagrams each illustrating a pixel circuit.
Figure 11B:
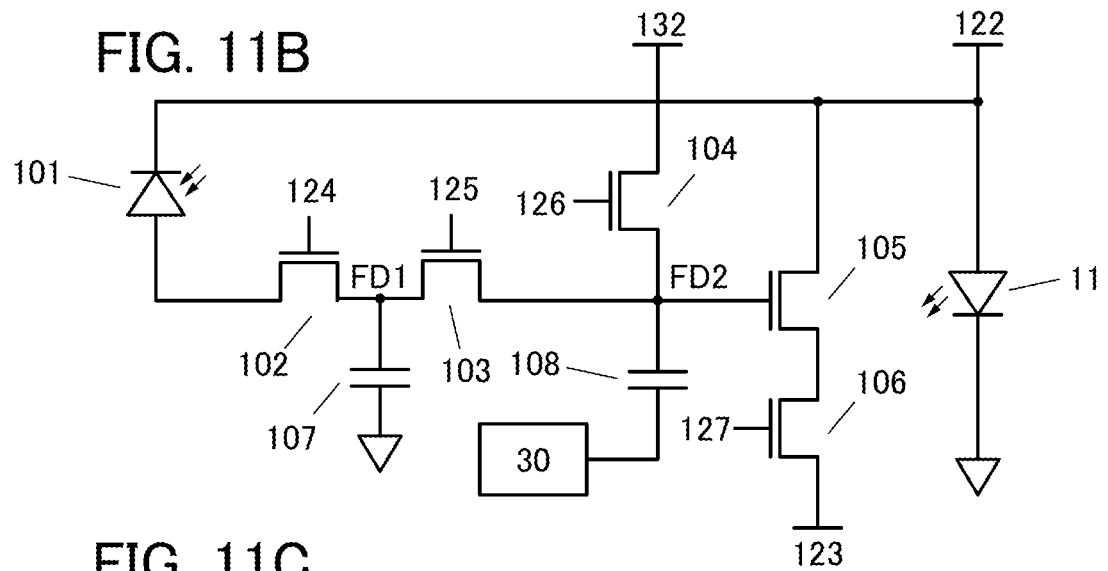
Figure 11C:
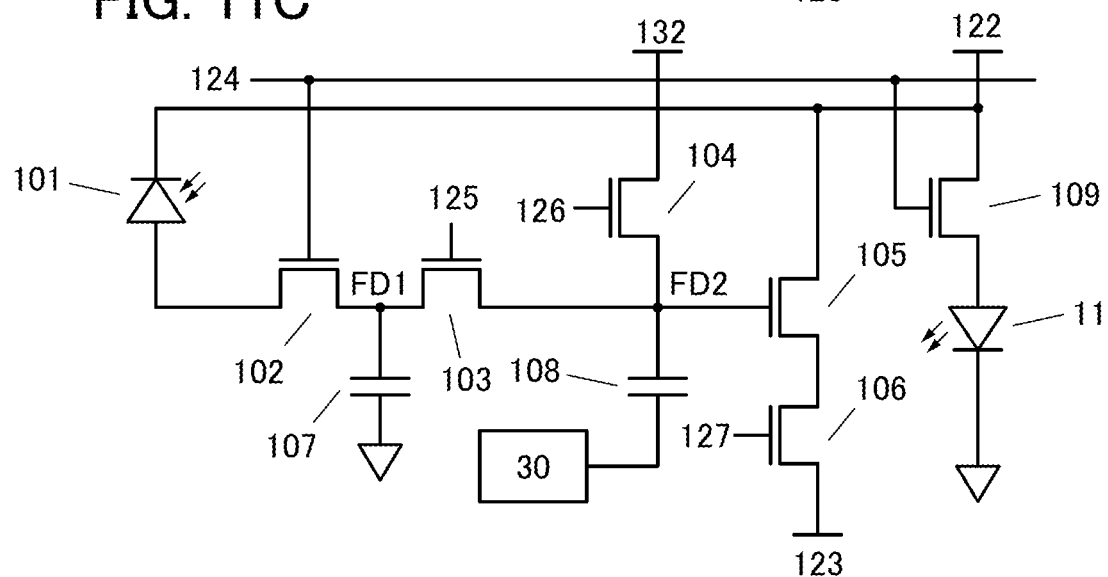
Figure 12A:
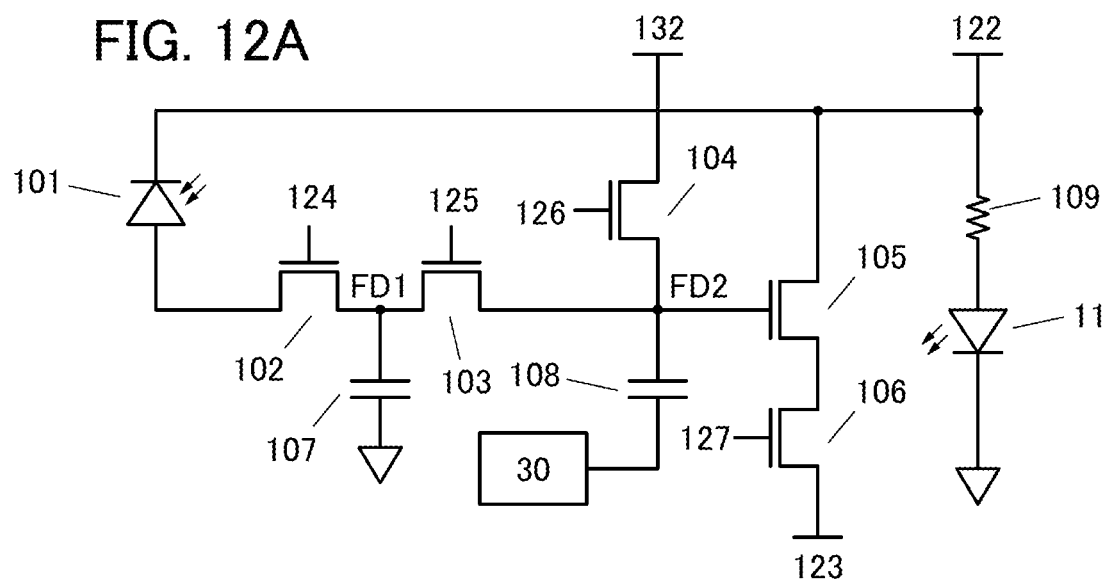
FIG. 12A to FIG. 12C are diagrams each illustrating a pixel circuit.
Figure 12B:
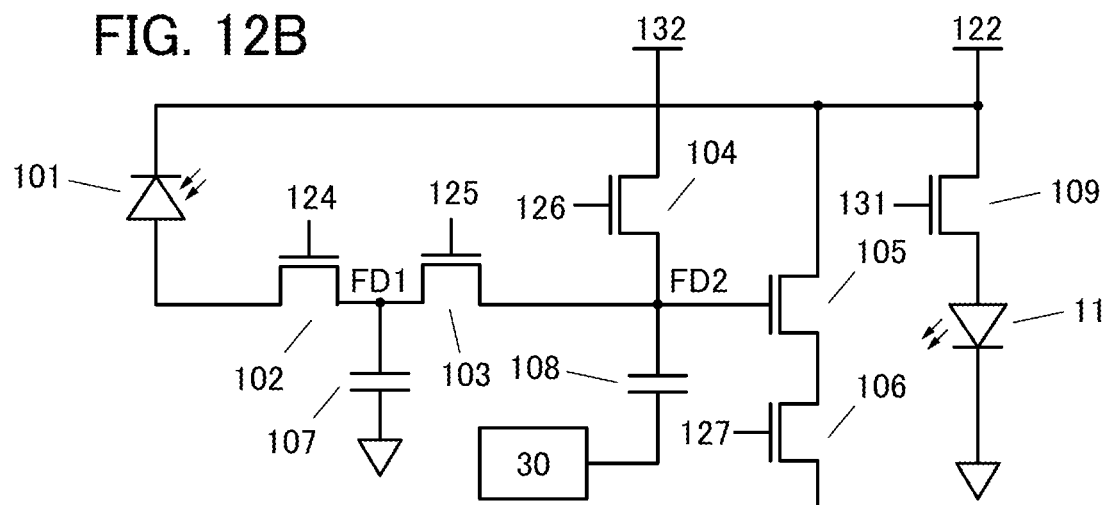
Figure 12C:
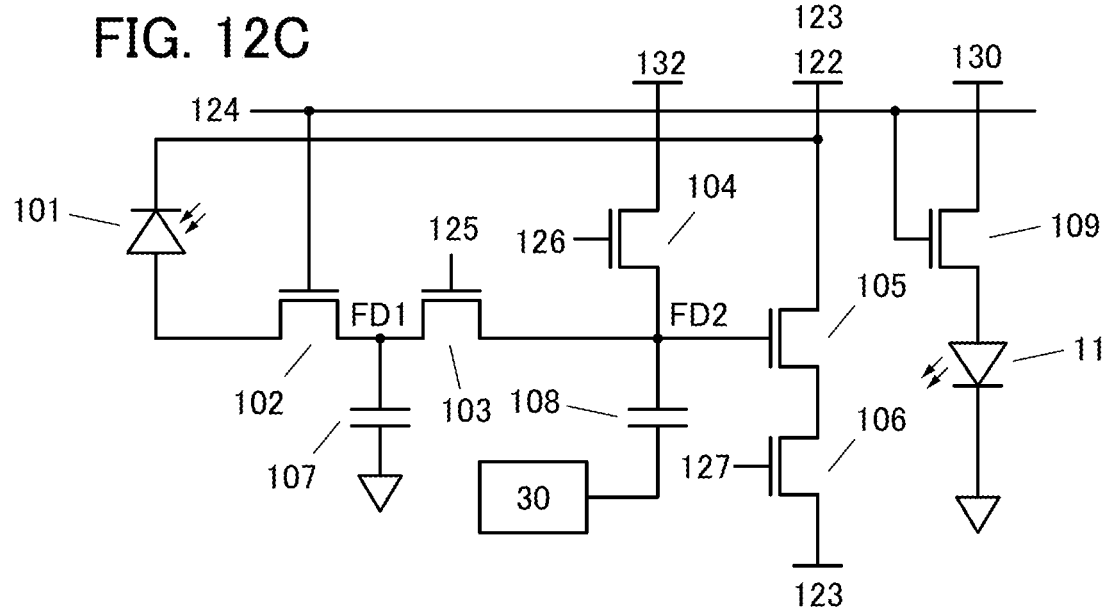

Furthermore, as illustrated in FIG. 10C, with the transistor 109 provided, the other of the source and the drain of the transistor 109 may be electrically connected to the wiring 130, and the gate of the transistor 109 may be electrically connected to the wiring 124. In this structure, the input potential to the light-emitting device 11 is controlled by the wiring 130, and the timing of light emission is controlled by the wiring 124.

Note that FIG. 9A to FIG. 9C and FIG. 10A to FIG. 10C show the configurations in which the cathode of the photoelectric conversion device 101 is electrically connected to the transistor 102. However, as illustrated in FIG. 11A to FIG. 11C and FIG. 12A to FIG. 12C, the anode of the photoelectric conversion device 101 may be electrically connected to the transistor 102.

In the configurations illustrated in FIG. 11A to FIG. 11C and FIG. 12A to FIG. 12C, the one electrode of the photoelectric conversion device 101 is electrically connected to the wiring 122 and the other electrode of the photoelectric conversion device 101 is electrically connected to the one of the source and the drain of the transistor 102. In addition, the other of the source and the drain of the transistor 104 is electrically connected to a wiring 132.

The wiring 132 can have a function of a power supply line or a supply line of a reset potential. In the configurations illustrated in FIG. 11A to FIG. 11C and FIG. 12A to FIG. 12C, the node FD1 and the node FD2 are reset to a low potential for the operation, and thus the wiring 132 is set to a low potential (a potential lower than that of the wiring 122).

For the connection between the light-emitting device 11 and the peripheral components illustrated in FIG. 11A to FIG. 11C and FIG. 12A to FIG. 12C, the descriptions for FIG. 9A to FIG. 9C and FIG. 10A to FIG. 10C can be referred to.

Figure 13A:
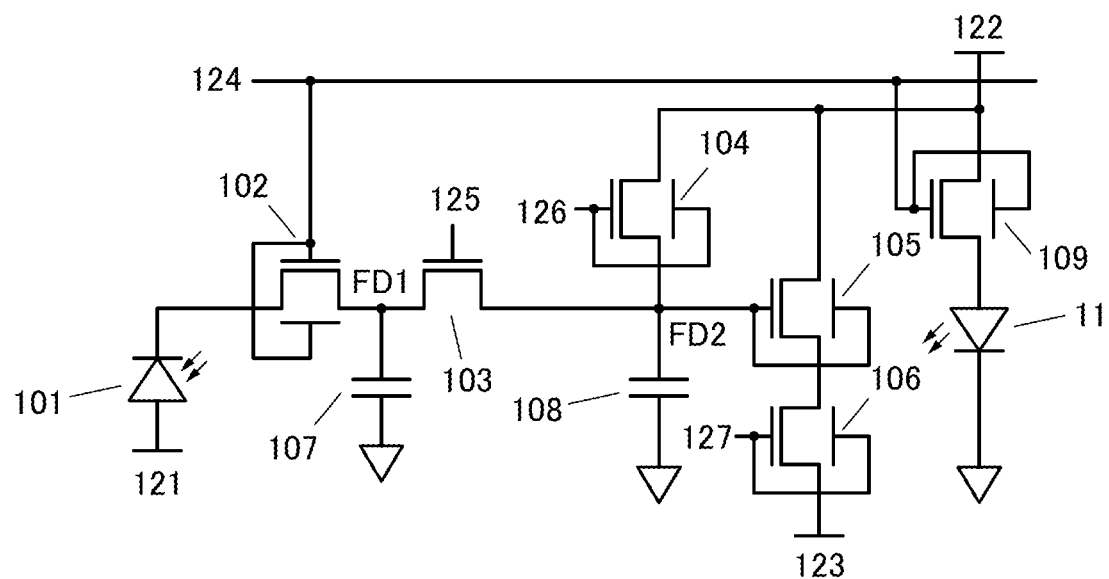
FIG. 13A and FIG. 13B are diagrams each illustrating a pixel circuit.
Figure 13B:
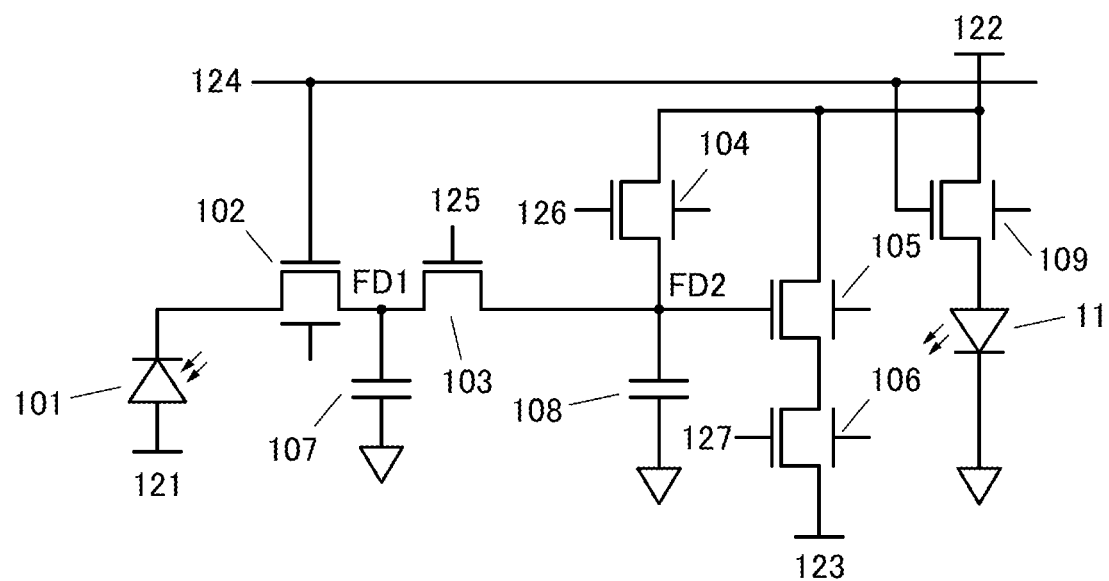

An OS transistor included in the imaging apparatus may be provided with a back gate. FIG. 13A shows a configuration in which back gates are electrically connected to front gates, which has an effect of increasing on-state currents. FIG. 13B shows a structure in which the back gates are each electrically connected to a wiring capable of supplying a constant potential, which enables the threshold voltage of the transistors to be controlled.

In addition, a configuration which enables each transistor to perform appropriate operation, for example, a configuration obtained by combination of FIG. 13A and FIG. 13B, may be employed. The pixel circuit may include a transistor not provided with a back gate. Note that a configuration with a transistor being provided with a back gate can be used in all the pixel circuits and peripheral circuits described in this embodiment.

This embodiment can be combined with any of the other embodiments as appropriate.

Embodiment 2

In this embodiment, structure examples and the like of the imaging apparatus of one embodiment of the present invention are described.

Figure 14A:
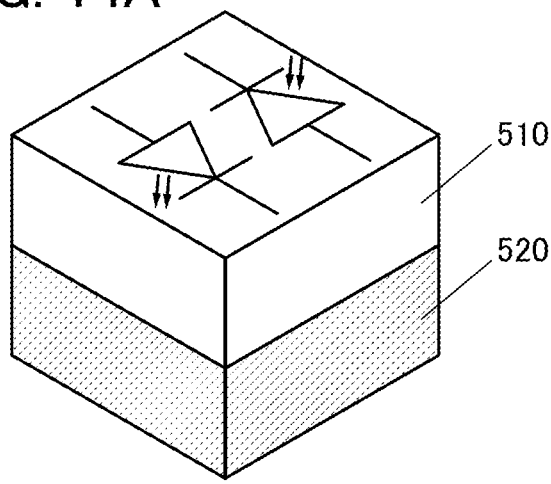
FIG. 14A to FIG. 14C are diagrams illustrating a structure of a pixel of an imaging apparatus, a structure of a photoelectric conversion device, and a structure of a light-emitting device.

FIG. 14A illustrates a structure example of a pixel included in the imaging apparatus. The pixel can have a stacked-layer structure composed of a layer 510 including the light-emitting device 11 and the photoelectric conversion device 101 and a layer 520 including transistors and the like that constitute the pixel circuit 10. Note that each of the layers includes a support substrate.

As the light-emitting device 11 included in the layer 510, a light-emitting device (EL element) that utilizes electroluminescence can be used. An EL element includes a layer containing a light-emitting compound (EL layer) between a pair of electrodes. By generating a potential difference between the pair of electrodes that is greater than the threshold voltage of the EL element, holes are injected into the EL layer from the anode side and electrons are injected into the EL layer from the cathode side. The injected electrons and holes are recombined in the EL layer and the light-emitting substance contained in the EL layer emits light.

EL elements are classified depending on whether a light-emitting material is an organic compound or an inorganic compound; in general, the former is referred to as an organic EL element, and the latter is referred to as an inorganic EL element.

In an organic EL element, voltage application causes electrons to be injected from one electrode to the EL layer and holes to be injected from the other electrode to the EL layer. Then, the carriers (electrons and holes) recombine, so that the light-emitting organic compound forms an excited state, and light is emitted when the excited state returns to a ground state. Owing to such a mechanism, this light-emitting device is referred to as a current-excitation light-emitting device.

The EL layer can be formed by a method such as an evaporation method (including a vacuum evaporation method), a transfer method, a printing method, an inkjet method, or a coating method.

Inorganic EL elements are classified according to their element structures into a dispersion-type inorganic EL element and a thin-film inorganic EL element. A dispersion-type inorganic EL element includes a light-emitting layer where particles of a light-emitting material are dispersed in a binder, and its light emission mechanism is donor-acceptor recombination type light emission that utilizes a donor level and an acceptor level. A thin-film inorganic EL element has a structure where a light-emitting layer is sandwiched between dielectric layers, which are further sandwiched between electrodes, and its light emission mechanism is localization type light emission that utilizes inner-shell electron transition of metal ions.

Figure 14B:
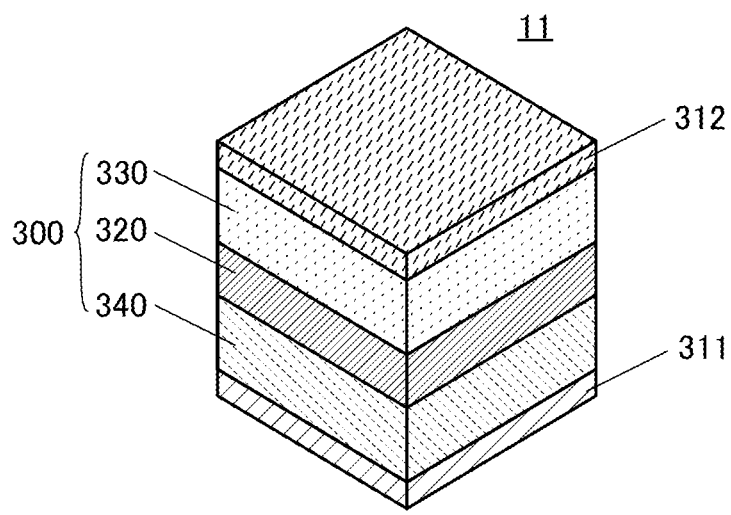

FIG. 14B illustrates a structure of the light-emitting device 11 (EL element). An EL layer 300 can include a plurality of layers such as a layer 330, a light-emitting layer 320, and a layer 340. The layer 330 can include a layer containing a substance having a high electron-injection property (an electron-injection layer), a layer containing a substance having a high electron-transport property (an electron-transport layer), and the like, for example. The light-emitting layer 320 contains a light-emitting compound, for example. The layer 340 can include a layer containing a substance having a high hole-injection property (a hole-injection layer) and a layer containing a substance having a high hole-transport property (a hole-transport layer), for example.

The EL layer 300 provided between an electrode 311 and an electrode 312 can function as a single light-emitting unit. Note that a plurality of light-emitting layers may be provided between the layer 330 and the layer 340. Note that a light-transmitting conductive film is used as either of the electrode 311 and the electrode 312, whereby the light emission direction is determined.

The light-emitting device 11 can emit light of various wavelengths depending on the material of the EL layer 300. In one embodiment of the present invention, a material that emits light having a peak in the near-infrared light (wavelengths from 720 to 2500 nm) is used as a material of the EL layer 300. For example, materials that emit light of 720 nm, 760 nm, 850 nm, 900 nm, 940 nm, and the vicinities of these wavelengths may be used in accordance with the uses.

Note that in one embodiment of the present invention, it is preferable that the EL layer 300 include an organometallic iridium complex that emits near-infrared light as the light-emitting material (also referred to as a guest material or a dopant material). The organometallic iridium complex preferably includes a dimethylphenyl skeleton and a quinoxaline skeleton. Furthermore, as the organometallic iridium complex, bis{4,6-dimethyl-2-[3-(3,5-dimethylphenyl)-2-quinoxalinyl-κN]phenyl-κC}(2,2',6,6'-tetramethyl-3,5-heptanedionato-κ$^2$O,O')iridium(III) (abbreviation: Ir(dmdpq)$_2$(dpm)) or the like can be typically used. With the use of the above-described organometallic iridium complex, it is possible to provide an imaging element with high quantum efficiency or high emission efficiency.

As the substance (i.e., a host material) used for dispersing the organometallic iridium complex, it is preferable to use a compound having an arylamine skeleton such as 2,3-bis(4-diphenylaminophenyl)quinoxaline (abbreviation: TPAQn) or NPB, a carbazole derivative such as CBP or 4,4',4"-tris(carbazol-9-yl)triphenylamine (abbreviation: TCTA), or a metal complex such as bis[2-(2'-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato) (4-phenyl phenolato)aluminum(III) (abbreviation: BAlq) or tris(8-quinolinolato)aluminum(III) (abbreviation: Alq$_3$), for example. In addition, a high molecular compound such as PVK can be used.

As the material (host material) used for dispersing the organometallic iridium complex, N-(1,1'-biphenyl-4-yl)-N-[4-(9-phenyl-9H-carbazol-3-yl)phenyl]-9,9-dimethyl-9H-fluoren-2-amine (abbreviation: PCBBiF) is suitably used.

Note that when the light-emitting layer 320 is formed so as to contain the above-described organometallic iridium complex (guest material) and the above-described host material, near-infrared phosphorescence can be obtained from the EL layer 300 with high emission efficiency.

As the photoelectric conversion device 101 included in the layer 510, a photodiode, a photoconductor, or the like can be used. The photoelectric conversion device 101 can be a stack including a layer 531, a layer 540, and a layer 532 as illustrated in FIG. 14C, for example.

Figure 14C:
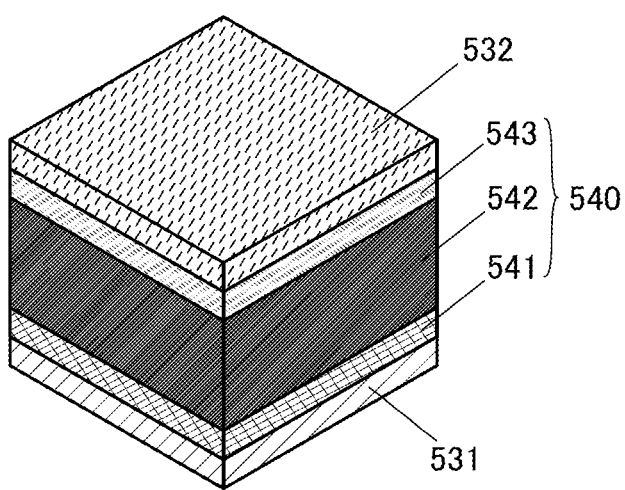

The photoelectric conversion device 101 illustrated in FIG. 14C is an example of an organic photoconductive film; the layer 531 and the layer 532 each correspond to an electrode, and one of them has a light-transmitting property so that light can be introduced into a photoelectric conversion portion. The layer 540 corresponds to the photoelectric conversion portion, and includes a layer 541, a layer 542, and the layer 542.

One of the layers 541 and 543 in the photoelectric conversion portion can be a hole-transport layer and the other can be an electron-transport layer. The layer 542 can be a photoelectric conversion layer.

For the hole-transport layer, molybdenum oxide can be used, for example. For the electron-transport layer, fullerene such as C60 or C70, or a derivative thereof can be used, for example.

As the photoelectric conversion layer, a mixed layer of an n-type organic semiconductor and a p-type organic semiconductor (bulk heterojunction structure) can be used. Examples of a material of the photoelectric conversion layer include organic semiconductor materials such as copper(II) phthalocyanine (CuPc) and tetraphenyldibenzoperiflanthene (DBP).

As the photoelectric conversion device 101, a pn-junction photodiode formed using single crystal silicon, a pin-junction photodiode formed using a thin film of single crystal silicon, microcrystalline silicon, polycrystalline silicon, or the like may be used, for example. Single crystal silicon, microcrystalline silicon, and polycrystalline silicon have infrared light sensitivity and is suitable for sensing of infrared light.

Components such as the transistors included in the pixel circuit 10 are mainly provided in the layer 520. Furthermore, some or all of the transistors included in the peripheral circuits described in Embodiment 1 may be included as well. An OS transistor is preferably used as the transistor.

As a semiconductor material used for an OS transistor, a metal oxide whose energy gap is greater than or equal to 2 eV, preferably greater than or equal to 2.5 eV, further preferably greater than or equal to 3 eV can be used. A typical example thereof is an oxide semiconductor containing indium; for example, a CAAC-OS or a CAC-OS, each of which will be described later, or the like can be used. A CAAC-OS has a crystal structure including stable atoms and is suitable for a transistor that is required to have high reliability, and the like. A CAC-OS has high mobility and is suitable for a transistor that operates at high speed, and the like.

In the OS transistor, a semiconductor layer has a large energy gap, and thus the OS transistor has an extremely low off-state current of several yoctoamperes per micrometer (current per micrometer of a channel width). The OS transistor has the following feature different from that of a Si transistor: impact ionization, an avalanche breakdown, a short-channel effect, or the like does not occur, and thus can configure a circuit having a high withstand voltage and high reliability. Moreover, variations in electrical characteristics due to crystallinity unevenness, which are caused in the Si transistor, are less likely to occur in the OS transistor.

The semiconductor layer included in the OS transistor can be, for example, a film represented by an In-M-Zn-based oxide that contains indium, zinc, and M (one or more of metals such as aluminum, titanium, gallium, germanium, yttrium, zirconium, lanthanum, cerium, tin, neodymium, or hafnium). The In-M-Zn-based oxide can be typically formed by a sputtering method. Alternatively, the In-M-Zn-based oxide may be formed by an ALD (Atomic layer deposition) method.

The atomic ratio of metal elements of a sputtering target used for forming the In-M-Zn oxide by a sputtering method preferably satisfies In≤M and Zn≤M The atomic ratio of metal elements in such a sputtering target is preferably, for example, In:M:Zn=1:1:1, In:M:Zn=1:1:1.2, In:M:Zn=3:1:2, In:M:Zn=4:2:3, In:M:Zn=4:2:4.1, In:M:Zn=5:1:6, In:M:Zn=5:1:7, or In:M:Zn=5:1:8. Note that the atomic ratio in the formed semiconductor layer varies from the above atomic ratios of metal elements of the sputtering target in a range of ±40%.

An oxide semiconductor with low carrier density is used for the semiconductor layer. For example, for the semiconductor layer, an oxide semiconductor whose carrier density is lower than or equal to $1\times10^{17}/cm^3$, preferably lower than or equal to $1\times10^{15}/cm^3$, further preferably lower than or equal to $1\times10^{13}/cm^3$, still further preferably lower than or equal to $1\times10^{11}/cm^3$, even further preferably lower than $1\times10^{10}/cm^3$, and higher than or equal to $1\times10^{-9}/cm^3$ can be used. Such an oxide semiconductor is referred to as a highly purified intrinsic or substantially highly purified intrinsic oxide semiconductor. The oxide semiconductor has a low density of defect states and can thus be referred to as an oxide semiconductor having stable characteristics.

Note that the composition is not limited to those described above, and an oxide semiconductor having the appropriate composition may be used depending on required semiconductor characteristics and electrical characteristics of the transistor (e.g., field-effect mobility and threshold voltage). To obtain the required semiconductor characteristics of the transistor, it is preferable that the carrier density, the impurity concentration, the defect density, the atomic ratio between a metal element and oxygen, the interatomic distance, the density, and the like of the semiconductor layer be set to appropriate values.

When silicon or carbon, which is one of elements belonging to Group 14, is contained in the oxide semiconductor contained in the semiconductor layer, oxygen vacancies are increased, and the semiconductor layer becomes n-type. Thus, the concentration of silicon or carbon (the concentration obtained by secondary ion mass spectrometry (SIMS)) in the semiconductor layer is set to lower than or equal to $2\times10^{18}$ atoms/$cm^3$, preferably lower than or equal to $2\times10^{17}$ atoms/$cm^3$.

Alkali metal and alkaline earth metal might generate carriers when bonded to an oxide semiconductor, in which case the off-state current of the transistor might be increased. Therefore, the concentration of alkali metal or alkaline earth metal in the semiconductor layer (the concentration obtained by SIMS) is set to lower than or equal to $1\times10^{18}$ atoms/$cm^3$, preferably lower than or equal to $2\times10^{16}$ atoms/$cm^3$.

When nitrogen is contained in the oxide semiconductor contained in the semiconductor layer, electrons serving as carriers are generated and the carrier density increases, so that the semiconductor layer easily becomes n-type. As a result, a transistor using an oxide semiconductor that contains nitrogen is likely to have normally-on characteristics. Hence, the nitrogen concentration (the concentration obtained by SIMS) in the semiconductor layer is preferably set to lower than or equal to $5\times10^{18}$ atoms/$cm^3$.

When hydrogen is contained in the oxide semiconductor contained in the semiconductor layer, hydrogen reacts with oxygen bonded to a metal atom to be water, and thus sometimes forms oxygen vacancies in the oxide semiconductor. When the channel formation region in the oxide semiconductor includes oxygen vacancies, the transistor sometimes has normally-on characteristics. In some cases, a defect in which hydrogen enters oxygen vacancies functions as a donor and generates electrons serving as carriers. In other cases, bonding of part of hydrogen to oxygen bonded to a metal atom generates electrons serving as carriers. Thus, a transistor using an oxide semiconductor that contains a large amount of hydrogen is likely to have normally-on characteristics.

A defect in which hydrogen enters oxygen vacancies can function as a donor of the oxide semiconductor. However, it is difficult to evaluate the defects quantitatively. Thus, the oxide semiconductor is sometimes evaluated by not its donor concentration but its carrier concentration. Therefore, in this specification and the like, the carrier concentration assuming the state where an electric field is not applied is sometimes used, instead of the donor concentration, as the parameter of the oxide semiconductor. That is, "carrier concentration" in this specification and the like can be replaced with "donor concentration" in some cases.

Therefore, hydrogen in the oxide semiconductor is preferably reduced as much as possible. Specifically, the hydrogen concentration of the oxide semiconductor, which is obtained by SIMS, is lower than $1\times10^{20}$ atoms/$cm^3$, preferably lower than $1\times10^{19}$ atoms/$cm^3$, further preferably lower than $5\times10^{18}$ atoms/$cm^3$, still further preferably lower than $1\times10^{18}$ atoms/$cm^3$. When an oxide semiconductor with sufficiently reduced impurities such as hydrogen is used for a channel formation region of a transistor, stable electrical characteristics can be given.

The semiconductor layer may have a non-single-crystal structure, for example. Examples of the non-single-crystal structure include CAAC-OS (C-Axis Aligned Crystalline Oxide Semiconductor) including a c-axis aligned crystal, a polycrystalline structure, a microcrystalline structure, and an amorphous structure. Among the non-single-crystal structures, the amorphous structure has the highest density of defect states, whereas the CAAC-OS has the lowest density of defect states.

An oxide semiconductor film having an amorphous structure has disordered atomic arrangement and no crystalline component, for example. Alternatively, an oxide film having an amorphous structure has, for example, a completely amorphous structure and no crystal part.

Note that the semiconductor layer may be a mixed film including two or more of a region having an amorphous structure, a region having a microcrystalline structure, a region having a polycrystalline structure, a CAAC-OS region, and a region having a single crystal structure. The mixed film has, for example, a single-layer structure or a stacked-layer structure including two or more of the above regions in some cases.

The composition of a CAC (Cloud-Aligned Composite)-OS, which is one embodiment of a non-single-crystal semiconductor layer, will be described below.

A CAC-OS refers to one composition of a material in which elements constituting an oxide semiconductor are unevenly distributed with a size greater than or equal to 0.5 nm and less than or equal to 10 nm, preferably greater than or equal to 1 nm and less than or equal to 2 nm, or a similar size, for example. Note that a state in which one or more metal elements are unevenly distributed and regions including the metal element(s) are mixed with a size greater than or equal to 0.5 nm and less than or equal to 10 nm, preferably greater than or equal to 1 nm and less than or equal to 2 nm, or a similar size in an oxide semiconductor is hereinafter referred to as a mosaic pattern or a patch-like pattern.

Note that an oxide semiconductor preferably contains at least indium. It is particularly preferable that indium and zinc be contained. Moreover, in addition to these, one kind or a plurality of kinds selected from aluminum, gallium, yttrium, copper, vanadium, beryllium, boron, silicon, titanium, iron, nickel, germanium, zirconium, molybdenum, lanthanum, cerium, neodymium, hafnium, tantalum, tungsten, magnesium, and the like may be contained.

For instance, a CAC-OS in an In—Ga—Zn oxide (an In—Ga—Zn oxide in the CAC-OS may be particularly referred to as CAC-IGZO) has a composition in which materials are separated into indium oxide (hereinafter, $InO_{X1}$ (X1 is a real number greater than 0)) or indium zinc oxide (hereinafter, $In_{X2}Zn_{Y2}O_{Z2}$ (X2, Y2, and Z2 are real numbers greater than 0)) and gallium oxide (hereinafter, $GaO_{X3}$ (X3 is a real number greater than 0)) or gallium zinc oxide (hereinafter, $Ga_{X4}Zn_{Y4}O_{Z4}$ (X4, Y4, and Z4 are real numbers greater than 0)), for example, so that a mosaic pattern is formed, and mosaic-like $InO_{X1}$ or $In_{X2}Zn_{Y2}O_{Z2}$ is evenly distributed in the film (which is hereinafter also referred to as cloud-like).

That is, the CAC-OS is a composite oxide semiconductor having a composition in which a region including $GaO_{X3}$ as a main component and a region including $In_{X2}Zn_{Y2}O_{Z2}$ or $InO_{X1}$ as a main component are mixed. Note that in this specification, for example, when the atomic ratio of In to an element M in a first region is larger than the atomic ratio of In to the element M in a second region, the first region is regarded as having a higher In concentration than the second region.

Note that IGZO is a commonly known name and sometimes refers to one compound formed of In, Ga, Zn, and O. A typical example is a crystalline compound represented by $InGaO_3(ZnO)_{m1}$ (m1 is a natural number) or $In_{(1+x0)}Ga_{(1-x0)}O_3(ZnO)_{m0}$ (−1≤x0≤1; m0 is a given number).

The above crystalline compound has a single crystal structure, a polycrystalline structure, or a CAAC structure. Note that the CAAC structure is a crystal structure in which a plurality of IGZO nanocrystals have c-axis alignment and are connected in the a-b plane without alignment.

On the other hand, the CAC-OS relates to the material composition of an oxide semiconductor. The CAC-OS refers to a composition in which, in the material composition containing In, Ga, Zn, and O, some regions that include Ga as a main component and are observed as nanoparticles and some regions that include In as a main component and are observed as nanoparticles are randomly dispersed in a mosaic pattern. Therefore, the crystal structure is a secondary element for the CAC-OS.

Note that the CAC-OS is regarded as not including a stacked-layer structure of two or more kinds of films with different compositions. For example, a two-layer structure of a film including In as a main component and a film including Ga as a main component is not included.

Note that a clear boundary cannot sometimes be observed between the region including $GaO_{X3}$ as a main component and the region including $In_{X2}Zn_{Y2}O_{Z2}$ or $InO_{X1}$ as a main component.

Note that in the case where one kind or a plurality of kinds selected from aluminum, yttrium, copper, vanadium, beryllium, boron, silicon, titanium, iron, nickel, germanium, zirconium, molybdenum, lanthanum, cerium, neodymium, hafnium, tantalum, tungsten, magnesium, and the like are contained instead of gallium, the CAC-OS refers to a composition in which some regions that include the metal element(s) as a main component and are observed as nanoparticles and some regions that include In as a main component and are observed as nanoparticles are randomly dispersed in a mosaic pattern.

The CAC-OS can be formed by a sputtering method under a condition where a substrate is not heated intentionally, for example. Moreover, in the case of forming the CAC-OS by a sputtering method, any one or more selected from an inert gas (typically, argon), an oxygen gas, and a nitrogen gas are used as a deposition gas. Furthermore, the ratio of the flow rate of an oxygen gas to the total flow rate of the deposition gas at the time of deposition is preferably as low as possible, and for example, the ratio of the flow rate of the oxygen gas is preferably higher than or equal to 0% and lower than 30%, further preferably higher than or equal to 0% and lower than or equal to 10%.

The CAC-OS is characterized in that no clear peak is observed in measurement using θ/2θ scan by an Out-of-plane method, which is one of X-ray diffraction (XRD) measurement methods. That is, it is found from the X-ray diffraction measurement that no alignment in the a-b plane direction and the c-axis direction is observed in a measured region.

In addition, in an electron diffraction pattern of the CAC-OS which is obtained by irradiation with an electron beam with a probe diameter of 1 nm (also referred to as a nanobeam electron beam), a ring-like high-luminance region (ring region) and a plurality of bright spots in the ring region are observed. It is therefore found from the electron diffraction pattern that the crystal structure of the CAC-OS includes an nc (nano-crystal) structure with no alignment in the plan-view direction and the cross-sectional direction.

Moreover, for example, it can be confirmed by EDX mapping obtained using energy dispersive X-ray spectroscopy (EDX) that the CAC-OS in the In—Ga—Zn oxide has a composition in which regions including $GaO_{X3}$ as a main component and regions including $In_{X2}Zn_{Y2}O_{Z2}$ or $InO_{X1}$ as a main component are unevenly distributed and mixed.

The CAC-OS has a composition different from that of an IGZO compound in which the metal elements are evenly distributed, and has characteristics different from those of the IGZO compound. That is, the CAC-OS has a composition in which regions including $GaO_{X3}$ or the like as a main component and regions including $In_{X2}Zn_{Y2}O_{Z2}$ or $InO_{X1}$ as a main component are phase-separated from each other and form a mosaic pattern.

Here, a region including $In_{X2}Zn_{Y2}O_{Z2}$ or $InO_{X1}$ as a main component is a region whose conductivity is higher than that of a region including $GaO_{X3}$ or the like as a main component. In other words, when carriers flow through the regions including $In_{X2}Zn_{Y2}O_{Z2}$ or $InO_{X1}$ as a main component, the conductivity of an oxide semiconductor is exhibited. Accordingly, when the regions including $In_{X2}Zn_{Y2}O_{Z2}$ or $InO_{X1}$ as a main component are distributed in an oxide semiconductor like a cloud, high field-effect mobility (μ) can be achieved.

By contrast, a region including $GaO_{X3}$ or the like as a main component is a region whose insulating property is higher than that of a region including $In_{X2}Zn_{Y2}O_{Z2}$ or $InO_{X1}$ as a main component. In other words, when regions including $GaO_{X3}$ or the like as a main component are distributed in an oxide semiconductor, leakage current can be suppressed and favorable switching operation can be achieved.

Accordingly, when the CAC-OS is used for a semiconductor element, the insulating property derived from $GaO_{X3}$ or the like and the conductivity derived from $In_{X2}Zn_{Y2}O_{Z2}$ or $InO_{X1}$ complement each other, whereby a high on-state current ($I_{on}$) and high field-effect mobility (μ) can be achieved.

A semiconductor element using the CAC-OS has high reliability. Thus, the CAC-OS is suitably used as a constituent material of a variety of semiconductor devices.

A flexible substrate is preferably used as the support substrate included in the layer 510 and the layer 520. When the support substrate is flexible, a flexible imaging apparatus can be fabricated. For example, it becomes easy for the imaging apparatus to be put on a living body by being firmly stuck to a portion of the living body.

As a material of the flexible support substrate, a polyester resin such as polyethylene terephthalate (PET) or polyethylene naphthalate (PEN), a polyacrylonitrile resin, an acrylic resin, a polyimide resin, a polymethyl methacrylate resin, a polycarbonate (PC) resin, a polyether sulfone (PES) resin, a polyamide resin (e.g., nylon or aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, or cellulose nanofiber can be used, for example.

As the support substrate included in the layer 520, a semiconductor substrate such as a silicon wafer, a glass substrate, a ceramic substrate, a metal substrate having an insulating surface, or the like may be used. These substrates are preferably processed to be thin enough to have flexibility. Depending on the use, a support substrate without flexibility may be used.

As the support substrate included in the layer 510, a substrate having a light-transmitting property with respect to light with a wavelength to be utilized can be selected from the above-described materials and used.

When a semiconductor substrate such as a silicon wafer is used as the support substrate included in the layer 520, a circuit for driving the pixel circuit, a read circuit of image signals, an image processing circuit, or the like can be provided over the semiconductor substrate.

Specifically, some or all of the transistors included in the circuits (the pixel circuit 10, the circuits 22, 23, and 28, and the like) described in Embodiment 1 can be provided over the support substrate. With such a structure, components of the pixel circuit and the peripheral circuits can be distributed in a plurality of layers and the components can be provided to overlap with each other or the components and the peripheral circuits can be provided to overlap with each other, whereby the area of the imaging apparatus can be reduced.

Figure 15:
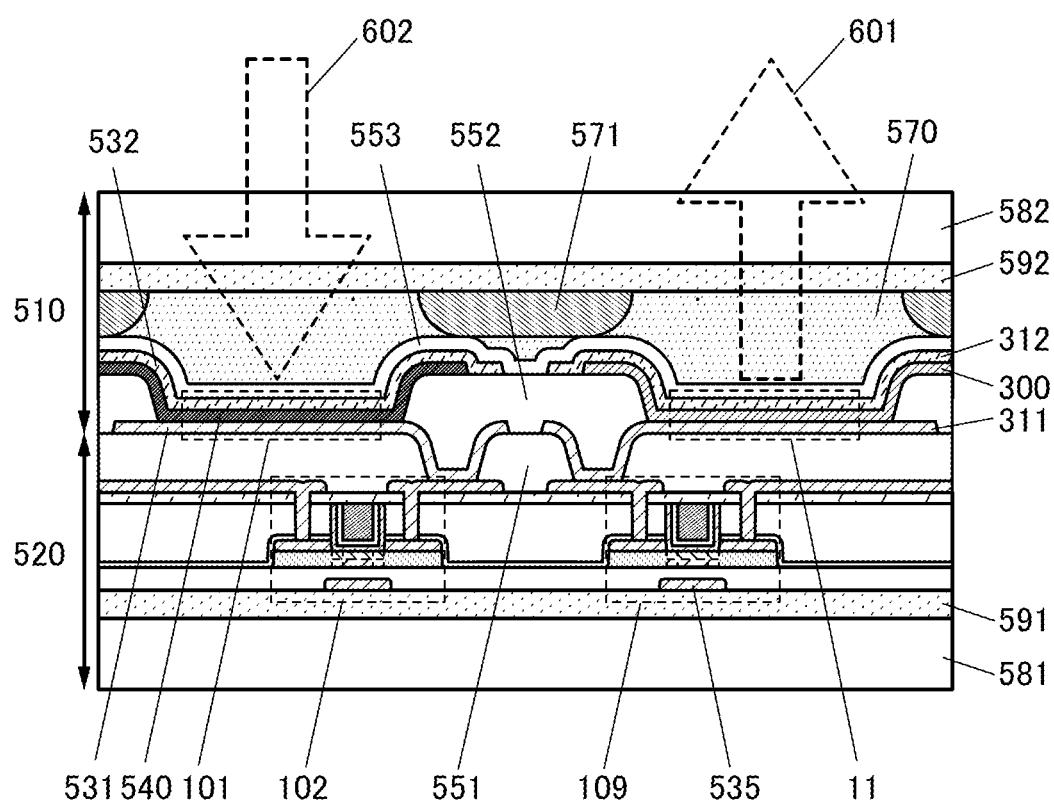
FIG. 15 is a diagram illustrating a structure of a pixel of an imaging apparatus.

FIG. 15 is a drawing illustrating an example of a cross section of the pixel shown in FIG. 14A. The layer 510 includes the EL element shown in FIG. 14B as the light-emitting device 11. The layer 510 also includes the organic photoconductive film shown in FIG. 14C as the photoelectric conversion device 101. The layer 520 includes OS transistors; in FIG. 15, the transistor 102 connected to the photoelectric conversion device 101 and the transistor 109 connected to the light-emitting device 11 are illustrated, taking the configuration shown in FIG. 9C as an example.

In the light-emitting device 11, the electrode 312 corresponds to the reference potential line (GND) shown in FIG. 9C. In the photoelectric conversion device 101, the layer 532 corresponds to a power supply line (wiring 121).

Figure 16A:
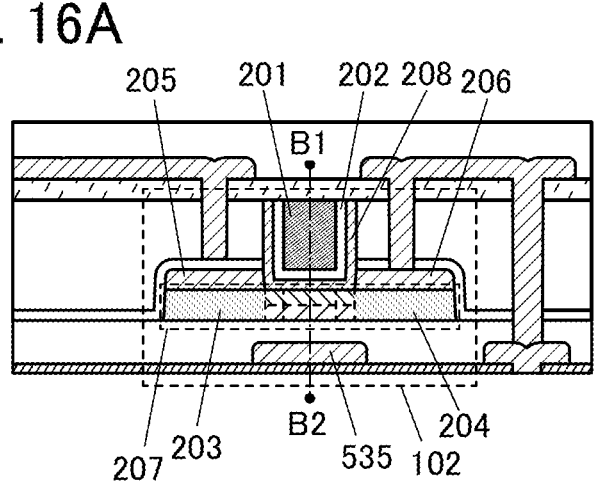
FIG. 16A to FIG. 16D are diagrams each illustrating a transistor.

The details of an OS transistor are shown in FIG. 16A. The OS transistor shown in FIG. 16A has a self-aligned structure; an insulating layer is provided over a stacked layer of an oxide semiconductor layer and a conductive layer, and a groove reaching the oxide semiconductor layer is provided, so that a source electrode 205 and the drain electrode 206 are formed.

The OS transistor can include a gate electrode 201 and a gate insulating film 202 in addition to a channel formation region, a source region 203, and a drain region 204, which are formed in an oxide semiconductor layer 207. At least the gate insulating film 202 and the gate electrode 201 are provided in the groove. The groove may further be provided with an oxide semiconductor layer 208.

Figure 16B:
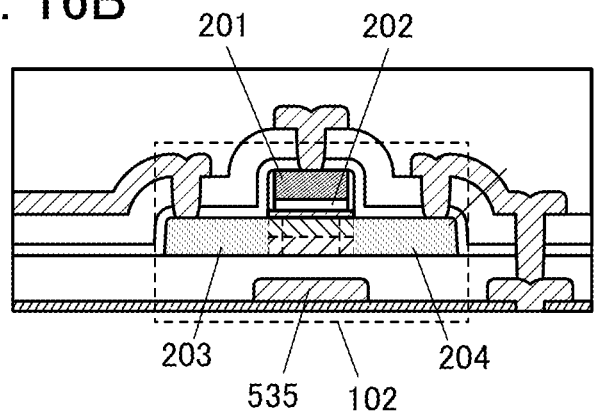

As shown in FIG. 16B, the OS transistor may have a self-aligned structure in which the source region 203 and the drain region 204 are formed in the semiconductor layer with the gate electrode 201 as a mask.

Figure 16C:
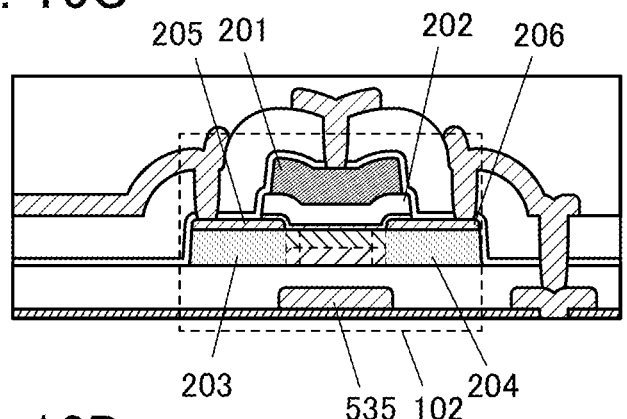

As shown in FIG. 16C, the OS transistor may be a non-self-aligned top-gate transistor including a region where the source electrode 205 or the drain electrode 206 overlaps with the gate electrode 201.

Figure 16D:
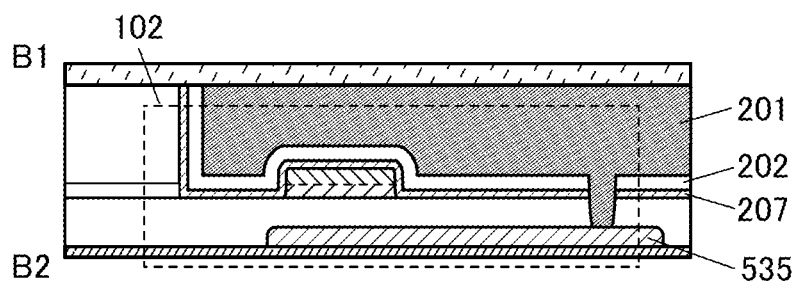

Although the transistors 102 and 109 each have a structure with a back gate 535, they may have a structure without a back gate. As illustrated in the cross-sectional view of the transistor in the channel width direction in FIG. 16D, the back gate 535 may be electrically connected to a front gate of the transistor, which is provided to face the back gate. Note that FIG. 16D illustrates the transistor of FIG. 16A as an example; however, the same applies to the transistors having the other structures. The back gate 535 may be supplied with a fixed potential that is different from that supplied to the front gate.

Over the transistors 102 and 109, planarization films 551 and 552 are provided. The light-emitting device 11 (the electrode 311, the EL layer 300, and the electrode 312) and the photoelectric conversion device 101 (the layer 531, the layer 540, and the layer 532) are provided over planar surfaces which are obtained owing to the planarization films 551 and 552 covering uneven portions generated at the transistors or the contact portion.

A low-resistance conductive film such as a metal can be used for the electrode 311 and the layer 531. For example, the electrode 311 and the layer 531 can be formed using one or more kinds selected from metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; or metal nitrides thereof.

As the electrode 312 and the layer 532, a light-transmitting conductive film that transmits near-infrared light can be used. For the electrode 312 and the layer 532, it is possible to use a conductive material with a light-transmitting property, such as indium oxide containing tungsten oxide, indium zinc oxide containing tungsten oxide, indium oxide containing titanium oxide, indium tin oxide, indium tin oxide containing titanium oxide, indium zinc oxide, or indium tin oxide to which silicon oxide is added, for example.

In the structure of the pixel illustrated in FIG. 15, the light-emitting device 11 included in the layer 510 emits light 601 to the outside, and reflected light 602 is received by the photoelectric conversion device 101 included in the layer 510.

A protective layer 553 may be provided over the light-emitting device 11 and the photoelectric conversion device 101 to prevent entry of oxygen, hydrogen, moisture, carbon dioxide, or the like into the light-emitting device 11 and the photoelectric conversion device 101. For the protective layer 553, an inorganic insulating film such as silicon nitride, silicon nitride oxide, aluminum oxide, aluminum nitride, aluminum oxynitride, aluminum nitride oxide, DLC (Diamond Like Carbon), or the like is preferably used.

In addition, it is preferable to provide a sealing layer 570 between the protective layer 553 and a substrate 582 for sealing. As the sealing layer 570, an ultraviolet curable resin or a thermosetting resin can be used as well as an inert gas such as nitrogen or argon; PVC (polyvinyl chloride), an acrylic resin, polyimide, an epoxy-based resin, a siliconebased resin, PVB (polyvinyl butyral), EVA (ethylene vinyl acetate), or the like can be used. A drying agent may also be contained in the sealing layer 570.

In addition, it is preferable to provide a light-blocking layer 571 at the boundary between the light-emitting device 11 and the photoelectric conversion device 101 and in the vicinity thereof, between the protective layer 553 and the substrate 582. Part of light emitted from the light-emitting device 11 is scattered or reflected by the sealing layer 570, the protective layer 553, the substrate 582, or the like, and received by the photoelectric conversion device 101 in some cases. The provision of the light-blocking layer 571 can prevent such stray light that does not contain useful information from being received by the photoelectric conversion device 101. The light-blocking layer 571 is preferably formed of a metal having a high reflectance or a resin having a high absorbance with respect to light with a wavelength to be utilized.

The substrates 581 and 582 are support substrates. In the case where flexible substrates are used as the substrates 581 and 582, a layer 591 is preferably provided between the substrate 581 and the region where the transistor and the like are provided. In addition, a layer 592 is preferably provided between the substrate 582 and the region where the sealing layer 570 is provided.

It is difficult to form a component that is formed at high temperatures and requires precise alignment (e.g., a transistor) directly onto a flexible substrate; such a component is commonly formed over a hard substrate first and then transferred to a flexible substrate. The layers 591 and 592 are buffer layers for peeling the component from the hard substrate, and can be formed using a resin with heat resistance and a small coefficient of linear expansion, such as polyimide, for example. Note that the layer 591 may have a function of a support substrate, without the substrate 581 being provided. In addition, the layer 592 may have a function of a support substrate, without the substrate 582 being provided.

This embodiment can be combined with any of the other embodiments as appropriate.

Embodiment 3

In this embodiment, examples of an electronic device in which the imaging apparatus of one embodiment of the present invention can be used are described.

FIG. 17A1 shows an infrared spectrometer that analyzes the brain function. As shown in FIG. 17A2, the infrared spectrometer is put on a human body such that the head is capped therewith. An imaging apparatus 912 of one embodiment of the present invention has flexibility, so that it can be attached to the inner curved surface of a helmet-shaped housing 911. Note that the imaging apparatus 912 may be attached to only a necessary portion of the housing 911, instead of the entire inner surface of the housing 911. The infrared spectrometer can include a data storing memory, a control LSI, a battery, or the like. Removal of data and supply of power can be performed through an external interface 913.

The infrared spectrometer is capable of detecting neural activity in the cerebral cortex by comparing (finding a difference between) the absorbance with respect to infrared light for which oxygenated hemoglobin has an absorption peak and the absorbance with respect to infrared light for which reduced hemoglobin has an absorption peak. An active portion in the brain and the intensity of the activity can be known, which can be used for understanding and research of injuries and diseases. The imaging apparatus 912 of one embodiment of the present invention includes a light source and is thin in shape; thus, a thin, lightweight infrared spectrometer can be formed.

FIG. 17B1 is an infrared spectrometer having basically the same function as but different shape and use from FIG. 17A1. The infrared spectrometer includes two imaging apparatuses 922 incorporated in a band 921, a battery 923, and a wireless communication unit 924. The infrared spectrometer is put on a portion of the head of a human body with the use of elasticity of the band 921, as shown in FIG. 17B2. The band 921 is formed of an elastic material such as a resin or a metal. Power can be supplied from the battery 923, and data can be transmitted or received through the wireless communication unit 924. The infrared spectrometer is small and lightweight, and can be used for detecting the activity of a specific part of the brain.

Figure 18A:
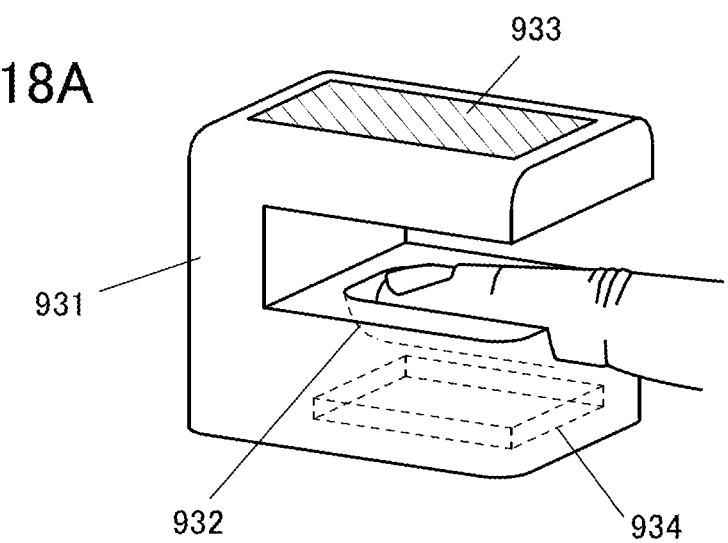
FIG. 18A and FIG. 18B are diagrams illustrating electronic devices.

FIG. 18A shows a pulse oximeter. With a finger being put on a detection portion 932 provided on a housing 931, an imaging device 934 placed right under the detection portion 932 captures the image. The result of image capturing is displayed on a display portion 933 provided on top of the housing 931. The pulse oximeter is capable of calculating an oxygen concentration in the blood from difference in absorbance between oxygenated hemoglobin and reduced hemoglobin with respect to light with two different wavelengths. The imaging apparatus 912 of one embodiment of the present invention includes a light source and is thin in shape; thus, a thin, lightweight pulse oximeter can be formed.

Figure 18B:
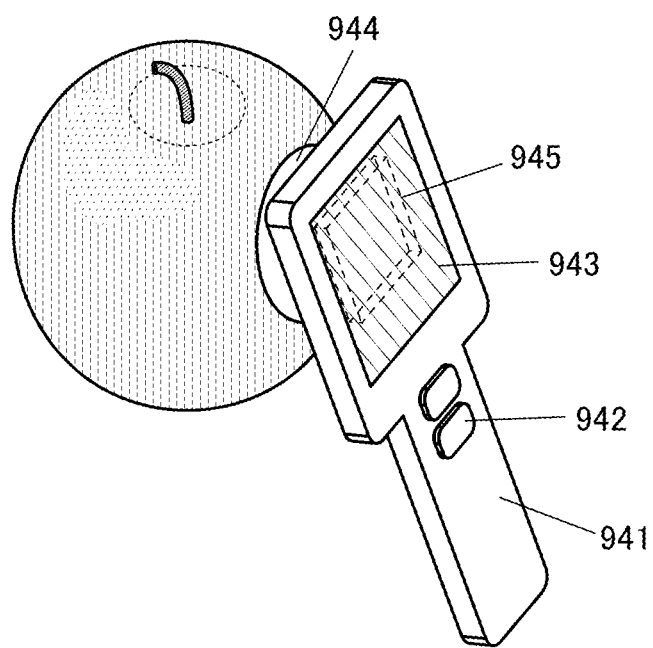

FIG. 18B shows a food screening device and includes a housing 941, an operation button 942, a display portion 943, a light-blocking hood 944, and the like. The light-blocking hood 944 provided in the periphery of the light-receiving portion is brought into intimate contact with a food of the inspection target, such as a fruit, and image capturing is performed; thus, a foreign body mixed into the food, a bug, a cavity or spoilage inside the food, and the like can be detected. In addition, an infrared spectroscopic spectrum can be obtained from difference between a plurality of infrared lights that are detected, whereby sugar content or the like of the food can also be detected. The food screening device can sort out defectives, classify foods according to the grade, and determine the harvest time. An imaging apparatus 945 of one embodiment of the present invention provided in the light receiving portion does not need an additional light source; therefore, a thin, lightweight, and highly portable food screening device can be formed at low costs.

This embodiment can be combined with any of the other embodiments as appropriate.

REFERENCE NUMERALS

10: pixel circuit, 11: light-emitting device, 11*a*: light-emitting device, 11*b*: light-emitting device, 11*c*: light-emitting device, 21: pixel array, 22: circuit, 23: circuit, 24: circuit, 25: circuit, 26: circuit, 27: circuit, 28: circuit, 29: current source circuit, 30: memory circuit, 101: photoelectric conversion device, 101*a*: photoelectric conversion device, 101*b*: photoelectric conversion device, 102: transistor, 103: transistor, 104: transistor, 105: transistor, 106: transistor, 107: capacitor, 108: capacitor, 109: transistor, 110: transistor, 111: transistor, 112: transistor, 113: transistor, 114: capacitor, 115: resistor, 121: wiring, 122: wiring, 123: wiring, 124: wiring, 125: wiring, 126: wiring, 127: wiring, 128: wiring, 130: wiring, 131: wiring, 132: wiring, 133: wiring, 134: wiring, 135: wiring, 136: wiring, 137: wiring, 138: wiring, 141: transistor, 142: transistor, 143: capacitor, 144: capacitor, 151: wiring, 152: wiring, 160: pixel, 170: pixel, 180: subject, 201: gate electrode, 202: gate insulating film, 203: source region, 204: drain region, 205: source electrode, 206: drain electrode, 207 oxide semiconductor layer, 208: oxide semiconductor layer, 300: EL layer, 311: electrode, 312: electrode, 320: light-emitting layer, 330: layer, 340: layer, 510: layer, 520: layer, 531: layer, 532: layer, 535: back gate, 540: layer, 541: layer, 542: layer, 543: layer, 551: planarization film, 552: planarization film, 553: protective layer, 570: sealing layer, 571: light-blocking layer, 581: substrate, 582: substrate, 591: layer, 592: layer, 601: light, 602: reflected light 911: housing, 912: imaging apparatus, 913: external interface, 921: band, 922: imaging apparatus, 923: battery, 924: wireless communication unit, 931: housing, 932: detection portion, 933: display portion, 934: imaging apparatus, 941: housing, 942: operation button, 943: display portion, 944: light-blocking hood, 945: imaging apparatus, This application is based on Japanese Patent Application Serial No. 2018-192666 filed with Japan Patent Office on Oct. 11, 2018, the entire contents of which are hereby incorporated herein by reference.

The invention claimed is:
1. An imaging apparatus comprising:
a first pixel;
a second pixel;
a first correlated double sampling circuit;
a second correlated double sampling circuit; and
an A/D converter circuit,
wherein the first pixel and the second pixel each comprise a light-emitting device and a photoelectric conversion device,
wherein the first pixel is electrically connected to the first correlated double sampling circuit,
wherein the second pixel is electrically connected to the first correlated double sampling circuit;
wherein the first correlated double sampling circuit is electrically connected to the second correlated double sampling circuit,
wherein the first correlated double sampling circuit is electrically connected to the A/D converter circuit through the second correlated double sampling circuit,
wherein the first pixel, the second pixel, the first correlated double sampling circuit, and the second correlated double sampling circuit comprise a transistor comprising a metal oxide in a channel formation region,
wherein the first pixel and the second pixel each comprise a first transistor as the transistor, a second transistor, a third transistor, a fourth transistor, and a fifth transistor,
wherein the first pixel and the second pixel each further comprise a first capacitor, a second capacitor, and a memory circuit,
wherein one of a source and a drain of the first transistor is electrically connected to one electrode of the photoelectric conversion device,
wherein the other of the source and the drain of the first transistor is electrically connected to one electrode of the first capacitor,
wherein the one electrode of the first capacitor is electrically connected to one of a source and a drain of the second transistor,
wherein the other of the source and the drain of the second transistor is electrically connected to one of a source and a drain of the third transistor,
wherein the one of the source and the drain of the third transistor is electrically connected to one electrode of the second capacitor,
wherein the one electrode of the second capacitor is electrically connected to a gate of the fourth transistor,
wherein one of a source and a drain of the fourth transistor is electrically connected to one of a source and a drain of the fifth transistor,
wherein the other of the source and the drain of the fifth transistor is electrically connected to the first correlated double sampling circuit, and
wherein the other electrode of the second capacitor is electrically connected to the memory circuit.

2. The imaging apparatus according to claim 1,
wherein the memory circuit comprises a sixth transistor, a seventh transistor, an eighth transistor, and a ninth transistor,
wherein the memory circuit further comprises a third capacitor,
wherein one of a source and a drain of the sixth transistor is electrically connected to one electrode of the third capacitor,
wherein the one electrode of the third capacitor is electrically connected to a gate of the seventh transistor,
wherein one of a source and a drain of the seventh transistor is electrically connected to one of a source and a drain of the eighth transistor,
wherein the other of the source and the drain of the seventh transistor is electrically connected to one of a source and a drain of the ninth transistor, and
wherein the one of the source and the drain of the ninth transistor is electrically connected to the other electrode of the second capacitor.

3. The imaging apparatus according to claim 1,
wherein the other of the source and the drain of the fifth transistor included in the first pixel and the other of the source and the drain of the fifth transistor included in the second pixel are electrically connected to each other, and
wherein a gate of the fifth transistor included in the first pixel and a gate of the fifth transistor included in the second pixel are electrically connected to each other.

4. The imaging apparatus according to claim 1,
wherein a first wavelength is shorter than a second wavelength,
wherein the light-emitting device included in the first pixel emits near-infrared light having a peak at the first wavelength,
wherein the light-emitting device included in the second pixel emits near-infrared light having a peak at the second wavelength, and
wherein the photoelectric conversion devices included in the first pixel and the second pixel have an absorption edge wavelength longer than or equal to the second wavelength.

5. The imaging apparatus according to claim 4,
wherein the first pixel comprises a first optical filter layer selectively transmitting light with the first wavelength or a neighborhood thereof, and
wherein the second pixel is provided with a second optical filter layer selectively transmitting light with the second wavelength or a neighborhood thereof.

6. The imaging apparatus according to claim 1,
wherein the first pixel, the second pixel, the first correlated double sampling circuit, and the second correlated double sampling circuit are between a first flexible substrate and a second flexible substrate facing the first flexible substrate.

7. The imaging apparatus according to claim 1,
wherein the metal oxide comprises In, Zn, and M, and
wherein M is Al, Tl, Ga, Ge, Sn, Y, Zr, La, Ce, Nd, or Hf.

8. An electronic device comprising the imaging apparatus according to claim 1 and a display apparatus.

9. An imaging apparatus comprising:
a first pixel;
a second pixel;
a first correlated double sampling circuit;
a second correlated double sampling circuit; and
an A/D converter circuit,
wherein the first pixel and the second pixel each comprise a light-emitting device and a photoelectric conversion device,
wherein the first pixel is electrically connected to the first correlated double sampling circuit,
wherein the second pixel is electrically connected to the first correlated double sampling circuit;
wherein the first correlated double sampling circuit is electrically connected to the second correlated double sampling circuit,
wherein the first correlated double sampling circuit is electrically connected to the A/D converter circuit through the second correlated double sampling circuit,
wherein the first pixel, the second pixel, the first correlated double sampling circuit, and the second correlated double sampling circuit comprise a transistor comprising a metal oxide in a channel formation region,
wherein a first wavelength is shorter than a second wavelength,
wherein the light-emitting devices included in the first pixel and the second pixel emit near-infrared light comprising the first wavelength and the second wavelength,
wherein the photoelectric conversion device included in the first pixel has an absorption edge wavelength shorter than the second wavelength, and
wherein the photoelectric conversion device included in the second pixel has an absorption edge wavelength longer than or equal to the second wavelength.

10. The imaging apparatus according to claim 9,
wherein the first pixel, the second pixel, the first correlated double sampling circuit, and the second correlated double sampling circuit are between a first flexible substrate and a second flexible substrate facing the first flexible substrate.

11. The imaging apparatus according to claim 9,
wherein the metal oxide comprises In, Zn, and M, and
wherein M is Al, Tl, Ga, Ge, Sn, Y, Zr, La, Ce, Nd, or Hf.

12. An electronic device comprising the imaging apparatus according to claim 9 and a display apparatus.

13. An imaging apparatus comprising:
a first pixel;
a second pixel;
a first correlated double sampling circuit;
a second correlated double sampling circuit; and
an A/D converter circuit,
wherein the first pixel and the second pixel each comprise a light-emitting device and a photoelectric conversion device,
wherein the first pixel is electrically connected to the first correlated double sampling circuit,
wherein the second pixel is electrically connected to the first correlated double sampling circuit;
wherein the first correlated double sampling circuit is electrically connected to the second correlated double sampling circuit,
wherein the first correlated double sampling circuit is electrically connected to the A/D converter circuit through the second correlated double sampling circuit,
wherein the first pixel, the second pixel, the first correlated double sampling circuit, and the second correlated double sampling circuit comprise a transistor comprising a metal oxide in a channel formation region,
wherein a first wavelength is shorter than a second wavelength,
wherein the light-emitting device included in the first pixel emits near-infrared light having a peak at the first wavelength,
wherein the light-emitting device included in the second pixel emits near-infrared light having a peak at the second wavelength,
wherein the photoelectric conversion device included in the first pixel has an absorption edge wavelength shorter than the second wavelength, and
wherein the photoelectric conversion device included in the second pixel has an absorption edge wavelength longer than or equal to the second wavelength.

14. The imaging apparatus according to claim 13,
wherein the first pixel, the second pixel, the first correlated double sampling circuit, and the second correlated double sampling circuit are between a first flexible substrate and a second flexible substrate facing the first flexible substrate.

15. The imaging apparatus according to claim 13,
wherein the metal oxide comprises In, Zn, and M, and
wherein M is Al, Tl, Ga, Ge, Sn, Y, Zr, La, Ce, Nd, or Hf.

16. An electronic device comprising the imaging apparatus according to claim 13 and a display apparatus.

* * * * *